United States Patent [19]

Nohira et al.

[11] Patent Number: 5,281,362
[45] Date of Patent: Jan. 25, 1994

[54] OPTICALLY ACTIVE COMPOUND, LIQUID CRYSTAL COMPOSITION, LIQUID CRYSTAL DEVICE, DISPLAY APPARATUS AND DISPLAY METHOD

[75] Inventors: Hiroyuki Nohira, Urawa; Takao Takiguchi, Tokyo; Takashi Iwaki, Machida; Takeshi Togano, Yokohama; Yoko Yamada; Shinichi Nakamura, both of Atsugi; Akira Sakaigawa, Urawa, all of Japan

[73] Assignee: Canon Kabushiki Kaisha, Tokyo, Japan

[21] Appl. No.: 834,390

[22] Filed: Feb. 12, 1992

[30] Foreign Application Priority Data

Feb. 13, 1991 [JP] Japan .................. 3-019938
Jan. 22, 1992 [JP] Japan .................. 4-009286

[51] Int. Cl.$^5$ ............... C09K 19/34; C09K 19/20; C07D 239/02; G02F 1/13
[52] U.S. Cl. .................. 252/299.61; 252/299.66; 252/299.67; 544/242; 544/298; 544/335; 359/103; 359/104
[58] Field of Search ........... 252/299.01, 299.61, 252/299.66, 299.67; 544/242, 298, 335; 359/103, 104

[56] References Cited

U.S. PATENT DOCUMENTS

| | | | |
|---|---|---|---|
| 4,367,924 | 1/1983 | Clark et al. | 350/334 |
| 4,917,817 | 4/1990 | Nohira et al. | 252/299.01 |
| 4,918,213 | 4/1990 | Nohira et al. | 558/271 |
| 5,073,306 | 12/1991 | Nohira et al. | 252/299.61 |

FOREIGN PATENT DOCUMENTS

| | | |
|---|---|---|
| 0293910 | 12/1988 | European Pat. Off. |
| 0301511 | 2/1989 | European Pat. Off. |
| 107216 | 8/1981 | Japan . |
| 1-31131 | 5/1989 | Japan . |
| 000127 | 1/1990 | Japan . |

OTHER PUBLICATIONS

Applied Physics Letters, vol. 18, No. 4 (1971) 127-28.

Primary Examiner—Robert L. Stoll
Assistant Examiner—Shean C. Wu
Attorney, Agent, or Firm—Fitzpatrick, Cella, Harper & Scinto

[57] ABSTRACT

An optically active compound represented by the following formula (I):

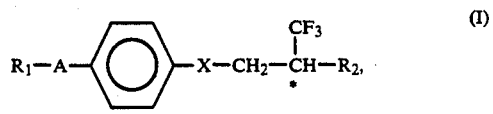

wherein $R_1$ denotes an alkyl or alkoxy group having 1-18 carbon atoms; $R_2$ denotes an alkyl group having 1-12 carbon atoms; A denotes

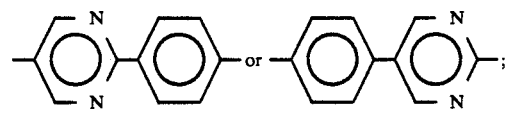

X denotes

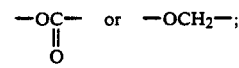

and C* denotes an optically active asymmetric carbon atom. The optically active compound, when included as a component, provides a ferroelectric liquid crystal composition or device showing an improved electrofield response characteristic.

28 Claims, 4 Drawing Sheets

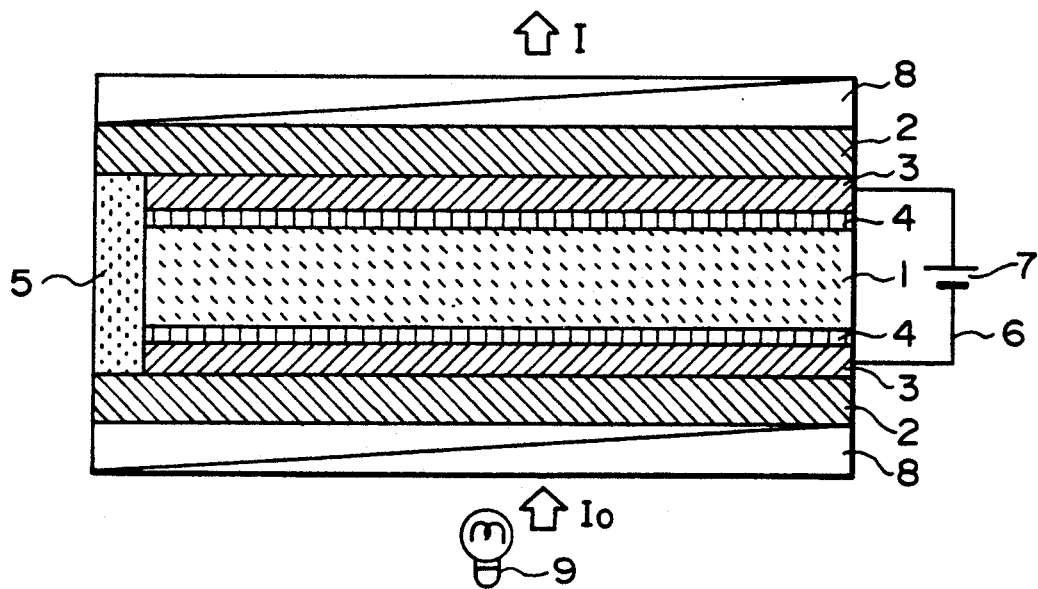
F I G. 1

OPTICALLY ACTIVE COMPOUND, LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to an optically active compound, a liquid crystal composition, a liquid crystal device, a display apparatus and a display method, and more particularly to a liquid crystal composition with improved responsiveness to an electric field, a liquid crystal device using the liquid crystal composition for use in a display device, a liquid crystal-optical shutter, etc., a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924. etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time $\gamma$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability Further, an excessively large spontaneous polarization is liable to accompany an increase in viscosity, so that remarkable increase in response speed may not be attained as a result.

Moreover, if it is assumed that the operation temperature of an actual display device is 5°-40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide an optically active compound, a liquid crystal composition, particularly a chiral smectic liquid crystal composition containing the mesomorphic compound for providing a practical ferroelectric liquid crystal device, a liquid crystal device using the liquid crystal composition and having a high response speed, a display apparatus using the device, and a display method using the composition and device.

According to the present invention, there is provided an optically active compound represented by the following formula (I):

$$R_1-A-\underset{}{\bigcirc}-X-CH_2-\underset{*}{\overset{CF_3}{\underset{|}{CH}}}-R_2, \quad (I)$$

wherein $R_1$ denotes an alkyl or alkoxy group having 1-18 carbon atoms; $R_2$ denotes an alkyl group having 1-12 carbon atoms; A denotes $$-\underset{N}{\overset{N}{\bigcirc}}-\bigcirc- \quad \text{or} \quad -\bigcirc-\underset{N}{\overset{N}{\bigcirc}}-;$$

X denotes $$-\underset{\overset{\|}{O}}{OC}- \quad \text{or} \quad -OCH_2-;$$

and C* denotes an optically active asymmetric carbon atom.

According to the present invention, there is further provided a liquid crystal composition containing at least one species of optically active compound as described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a liquid crystal composition assuming a chiral smectic phase;

DETAILED DESCRIPTION OF THE INVENTION

Figure 2:
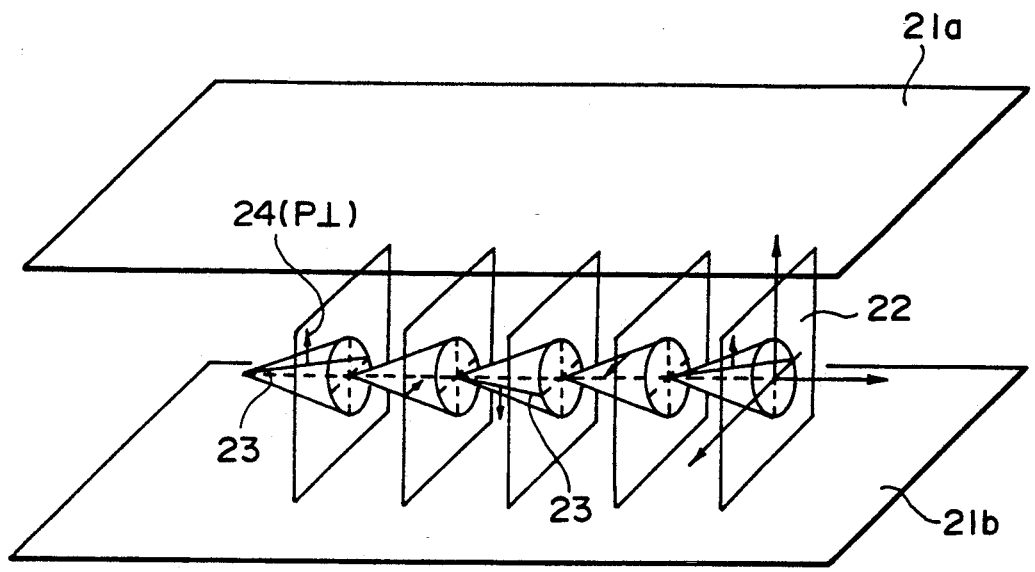
FIGS. 2 and 3 are schematic perspective views of a device cell embodiment for illustrating the operation principle of a liquid crystal device utilizing ferroelectricity of a liquid crystal composition.

In the formula (I) as described above, Preferred examples of $R_1$ may include an alkyl or alkoxy group having 3-14 carbon atoms.

Preferred examples of $R_2$ may include an n-alkyl group having 4-8 carbon atoms.

The optically active compound represented by the above-mentioned formula (I) is characterized by a partial three-rings structure connected by a single bond to one another. The compound with such a structure has a good electric field-response characteristic similarly as in a compound disclosed by Japanese Laid-Open patent Application (JP-A) No. 127/1990. A liquid crystal composition containing the compound of the formula (I) of the present invention provides not only a high speed responsiveness but also a small temperature-dependence of response speed.

The above compound of the formula (I) may preferably produced through optically active intermediates such as 3-trifluoromethyl-1-heptanoic acid of the formula (II) below and 3-trifluoromethyl-1-heptanol of the formula (III) below as disclosed in Japanese Patent Application Nos. 183485/1987 and 4/1988 and U.S. Pat. No. 4,917,817.

$$R-\underset{*}{\overset{CF_3}{\underset{|}{CH}}}-CH_2\underset{\overset{\|}{O}}{C}-OH \quad (II)$$

$$R-\underset{*}{\overset{CF_3}{\underset{|}{CH}}}-CH_2CH_2OH \quad (III)$$

The optically active compound of the above-mentioned formula (I) may generally be synthesized through the following reaction schemes A and B.

Scheme A

Case where X = —OC—
                  ‖
                  O

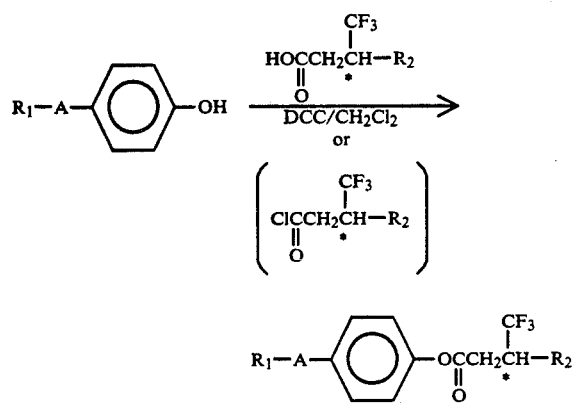

Scheme B

Case where X = —OCH₂—

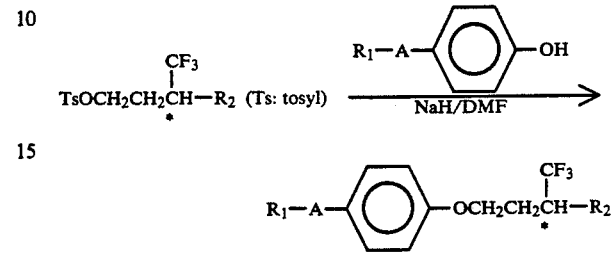

In the above, R₁, R₂ and A are the same as defined in the above formula (I), respectively.

Specific examples of the optically active compounds represented by the formula (I) may include those shown in the following structural formulas.

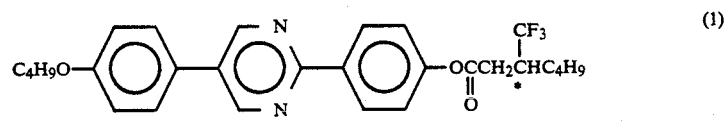 (1)

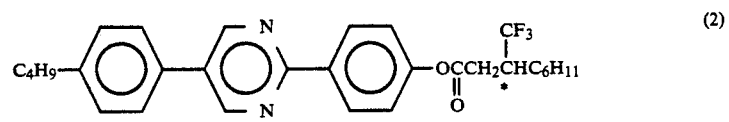 (2)

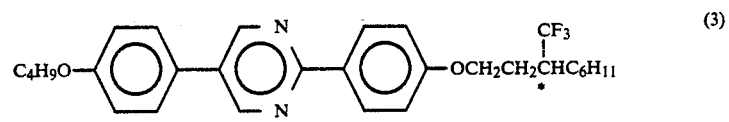 (3)

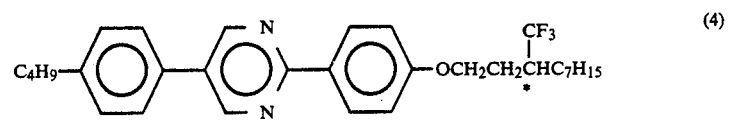 (4)

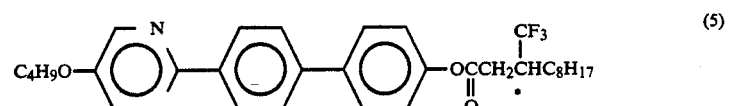 (5)

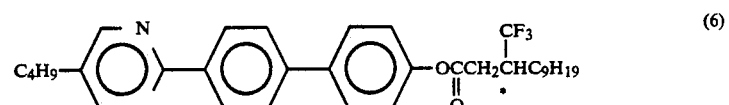 (6)

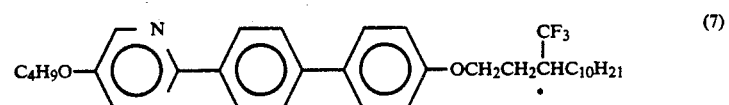 (7)

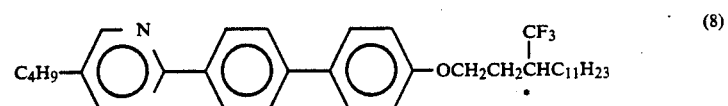 (8)

-continued
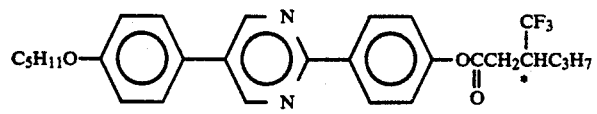 (9)
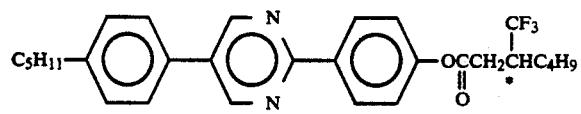 (10)
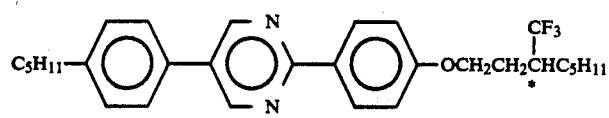 (11)
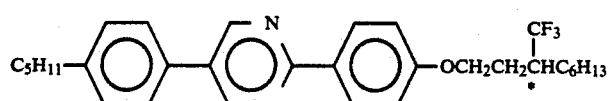 (12)
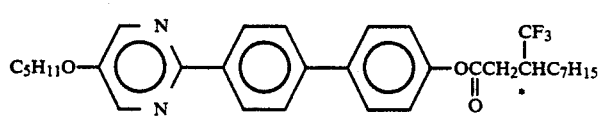 (13)
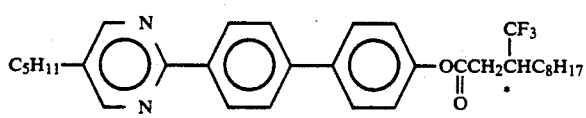 (14)
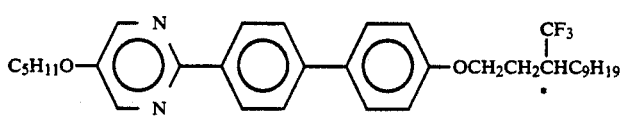 (15)
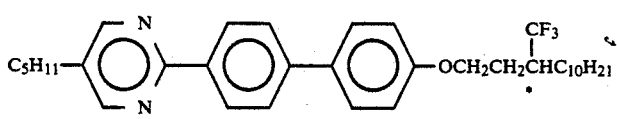 (16)
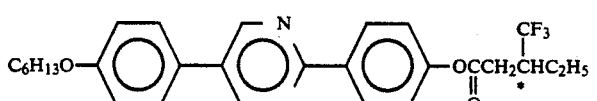 (17)
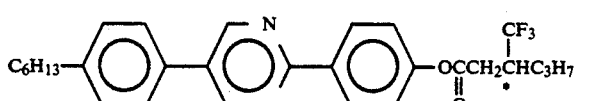 (18)
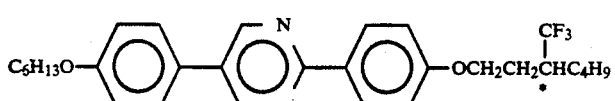 (19)
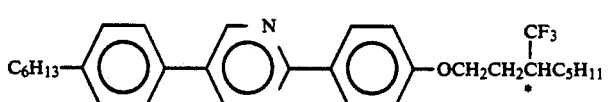 (20)
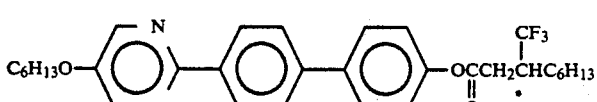 (21)

-continued
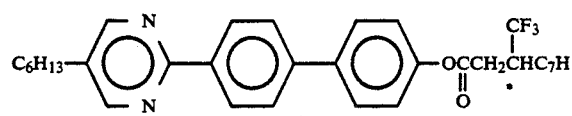 (22)
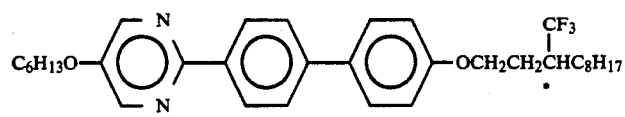 (23)
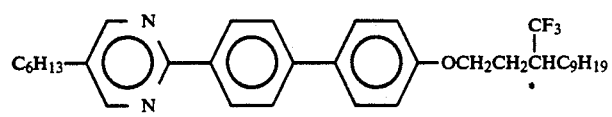 (24)
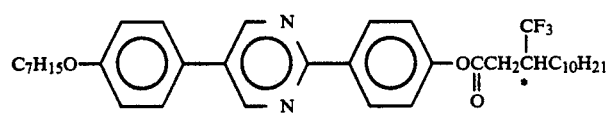 (25)
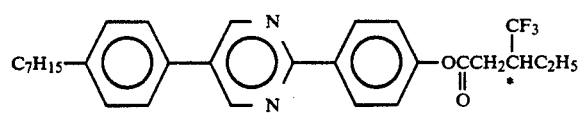 (26)
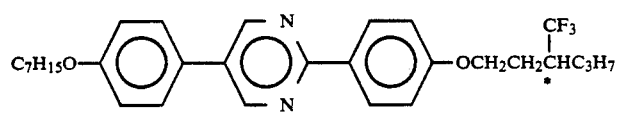 (27)
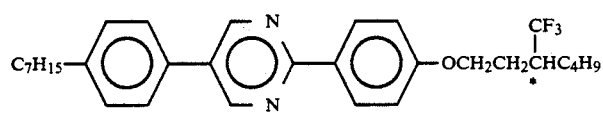 (28)
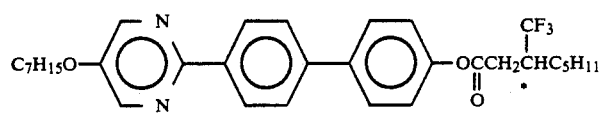 (29)
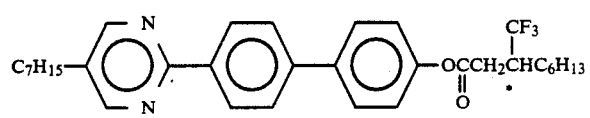 (30)
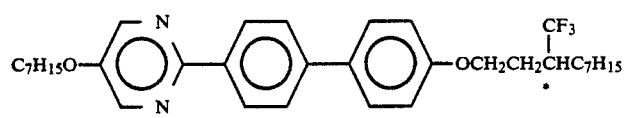 (31)
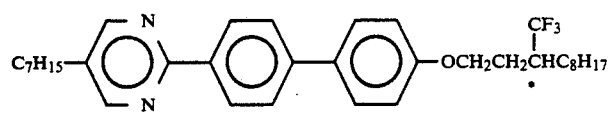 (32)
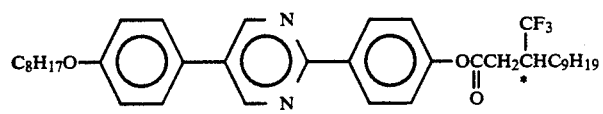 (33)
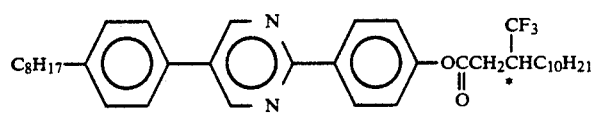 (34)

-continued
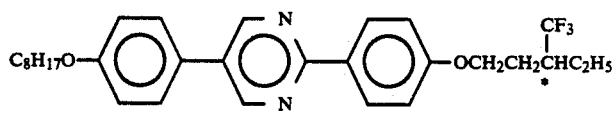 (35)
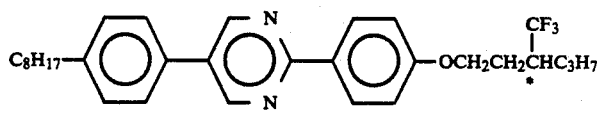 (36)
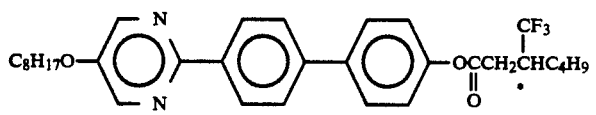 (37)
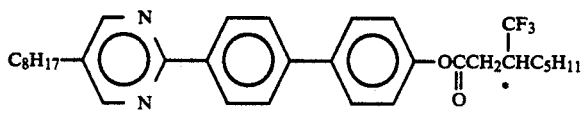 (38)
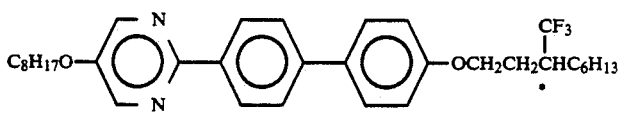 (39)
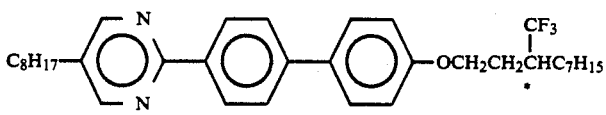 (40)
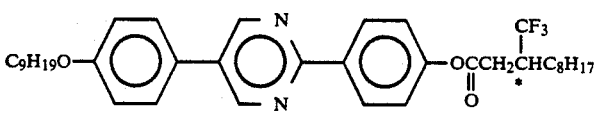 (41)
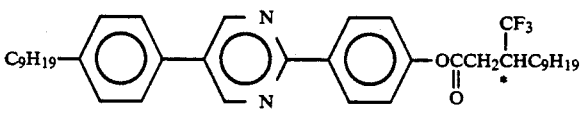 (42)
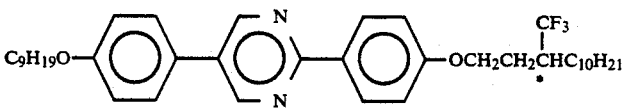 (43)
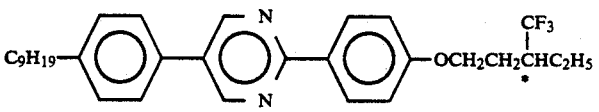 (44)
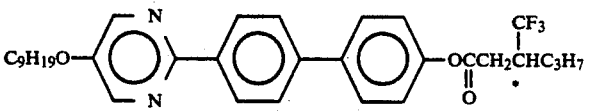 (45)
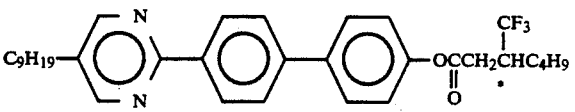 (46)
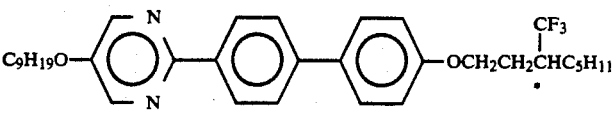 (47)

-continued
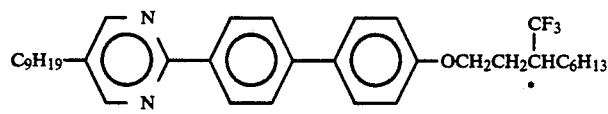 (48)
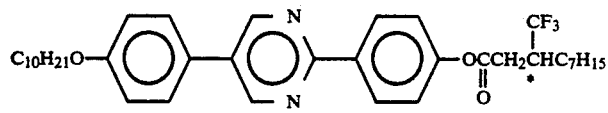 (49)
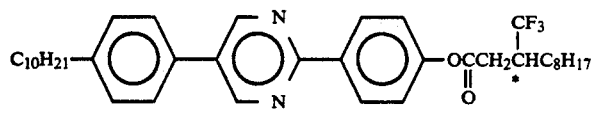 (50)
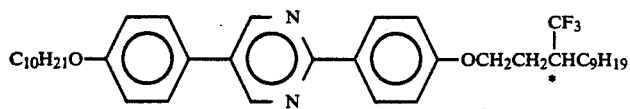 (51)
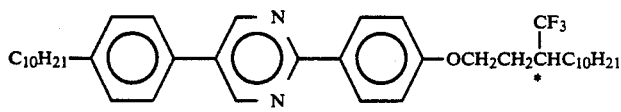 (52)
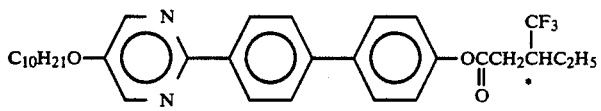 (53)
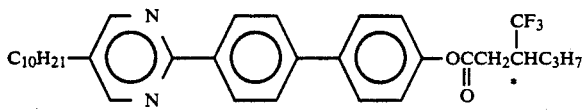 (54)
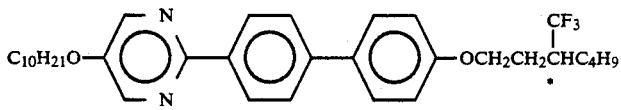 (55)
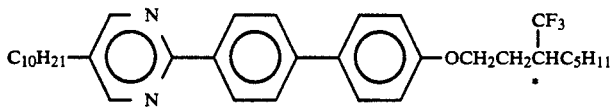 (56)
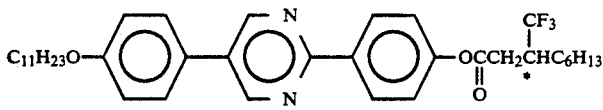 (57)
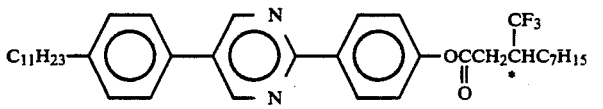 (58)
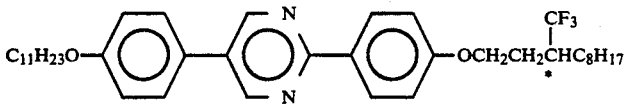 (59)
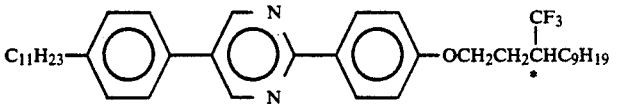 (60)

-continued
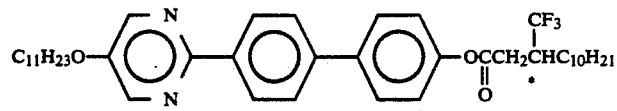 (61)
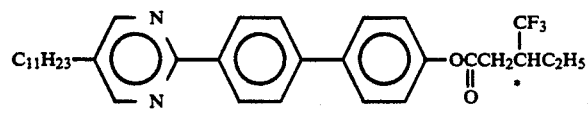 (62)
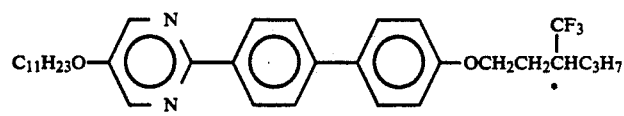 (63)
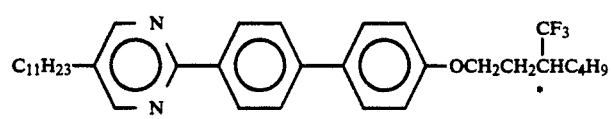 (64)
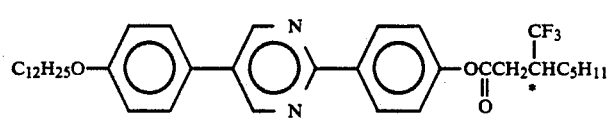 (65)
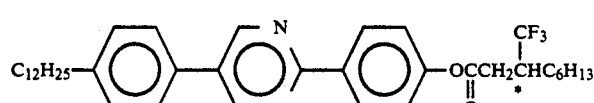 (66)
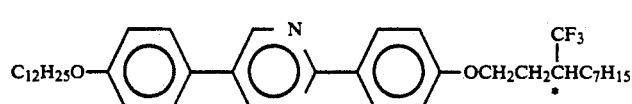 (67)
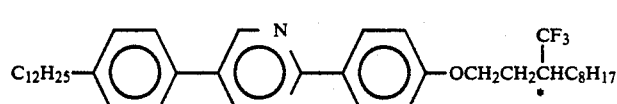 (68)
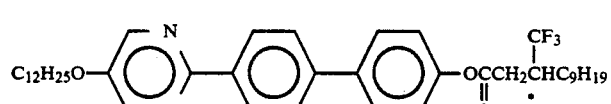 (69)
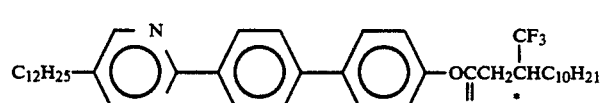 (70)
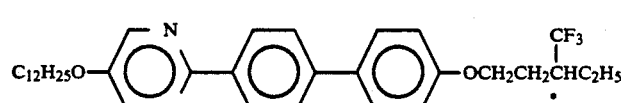 (71)
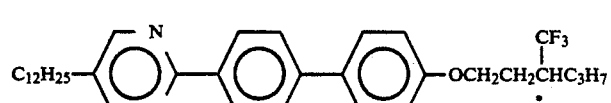 (72)
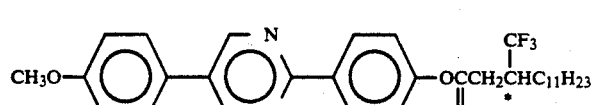 (73)

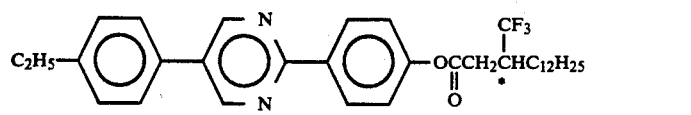 (74)
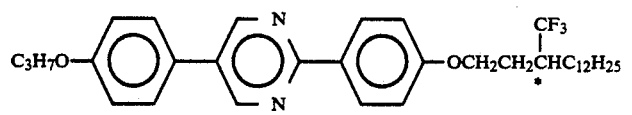 (75)
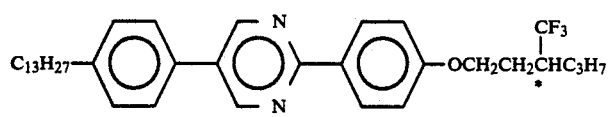 (76)
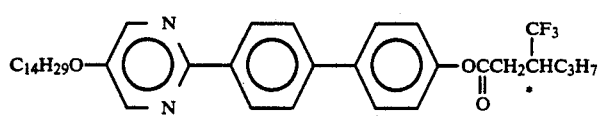 (77)
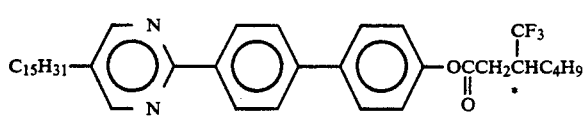 (78)
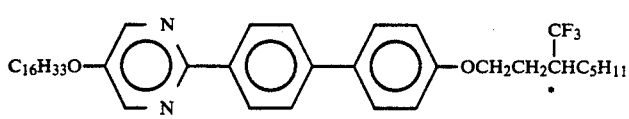 (79)
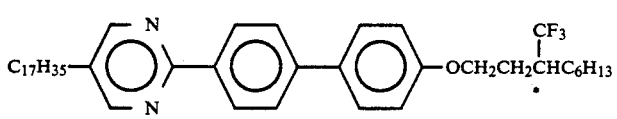 (80)
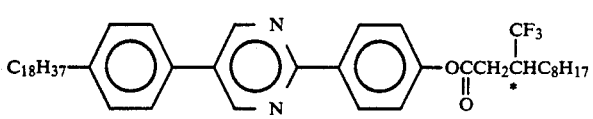 (81)
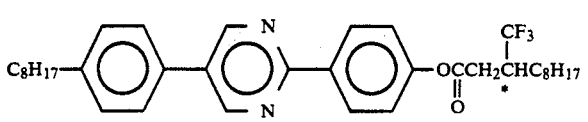 (82)
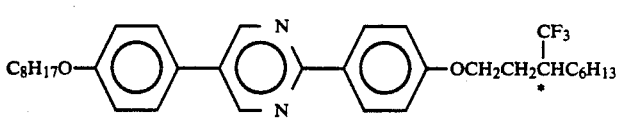 (83)
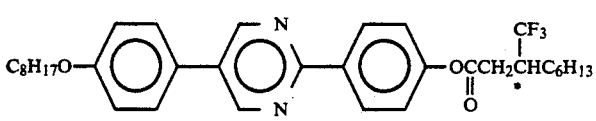 (84)
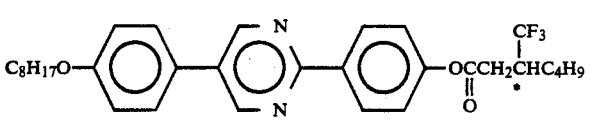 (85)
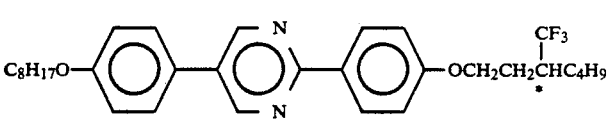 (86)

-continued

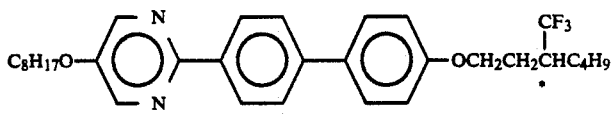 (87)

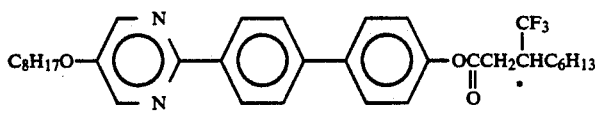 (88)

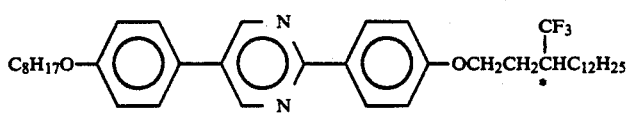 (89)

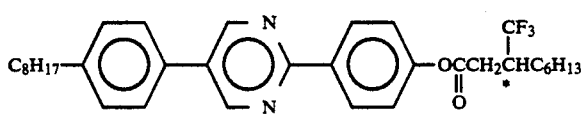 (90)

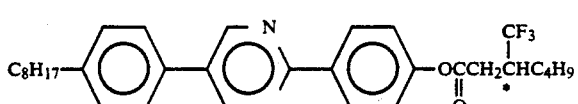 (91)

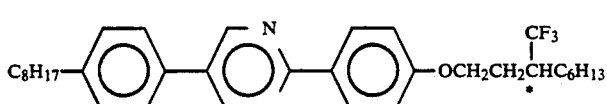 (92)

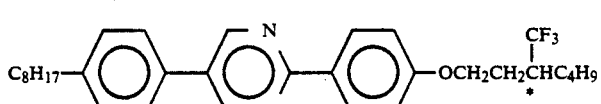 (93)

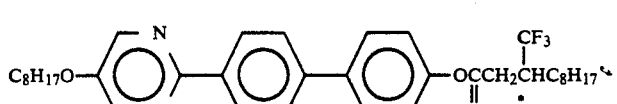 (94)

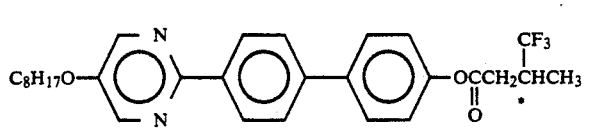 (95)

The liquid crystal composition according to the present invention may be obtained by mixing at least one species of the compound represented by the formula (I) and at least one species of another mesomorphic compound in appropriate proportions. The liquid crystal composition according to the present invention may preferably be formulated as a liquid crystal composition capable of showing ferroelectricity, particularly a liquid crystal composition showing a chiral smectic phase.

Specific examples of another mesomorphic compound as described above may include those denoted by the following formulas (III) to (XII).

wherein e denotes 0 or 1 and f denotes 0 or 1 with proviso that $e+f=0$ or 1; Y' denotes H, halogen, $CH_3$ or $CF_3$; $X_1'$ and $X_2'$ respectively denote a single bond,

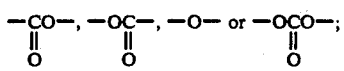

and $X_3'$ and $X_4'$ respectively denote a single bond,

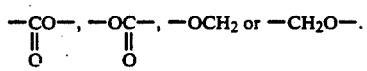

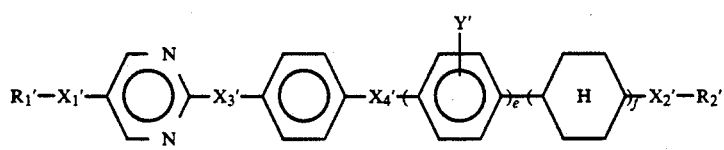 (III)

In the formula (III), preferred compounds thereof may include those represented by the following formulas (IIIa) to (IIId):

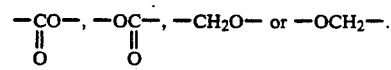

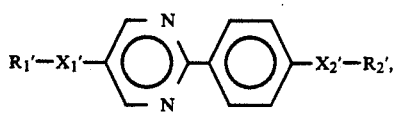
(IIIa)

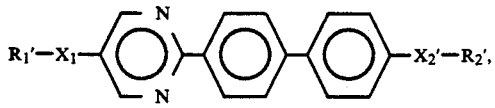
(IIIb)

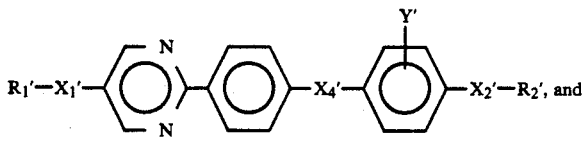
(IIIc)

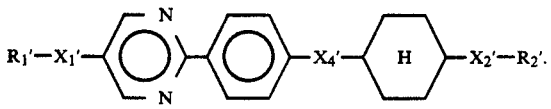
(IIId)

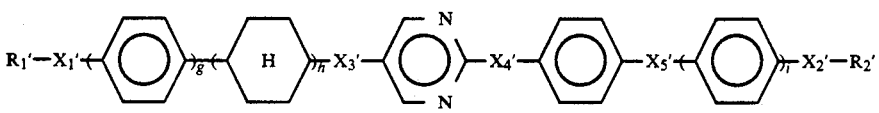
(IV)

wherein g and h respectively denote 0 or 1 with proviso that g+h=1; i denotes 0 or 1; $X_1'$ and $X_2'$ respectively denote a single bond, In the formula (IV), preferred compounds thereof may include those represented by the following formulas (IVa) to (IVc):

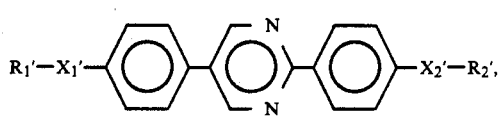
(IVa)

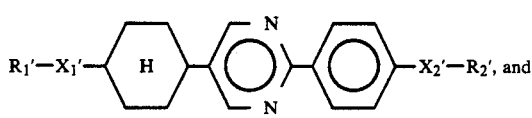
(IVb)

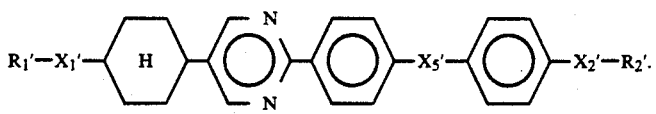
(IVc)

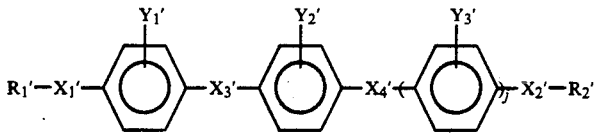
(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond,

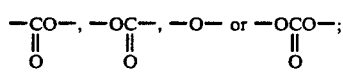

and $X_3'$, $X_4'$ and $X_5'$ respectively denote a single bond,

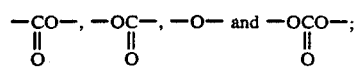

and $X_3'$ and $X_4'$ respectively denote a single bond,

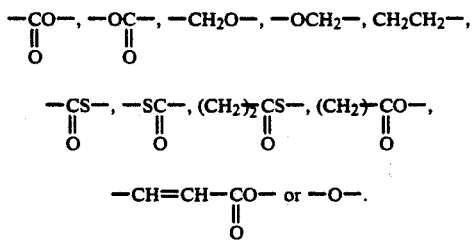

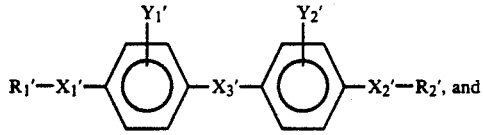

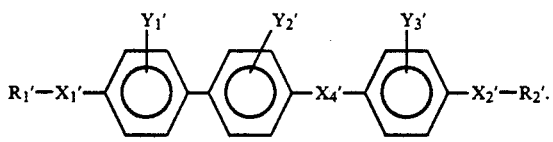

In the formula (V), preferred compounds thereof may include those represented by the following formulas (Va) and (Vb):

(Va)
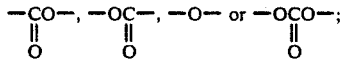

(Vb)
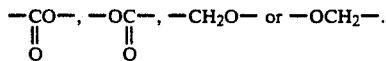

(VI)
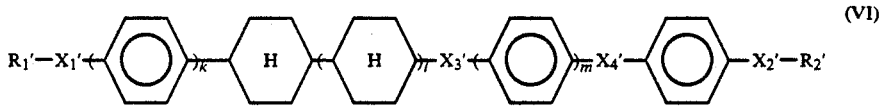

wherein k, l and m respectively denote 0 or 1 with proviso that $k+l+m=0$, 1 or 2; $X_1'$ and $X_2'$ respectively denote a single bond,

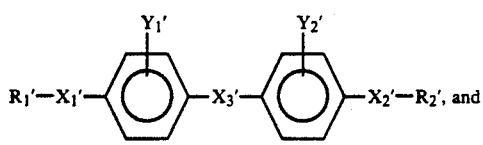

and $X_3'$ and $X_4'$ respectively denote a single bond,

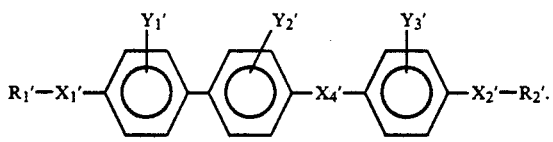

In the formula (VI), preferred compounds thereof may include those represented by the following formulas (VIa) to (VIf):

(VIa)
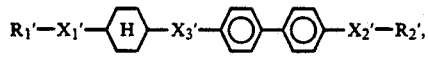

(VIb)
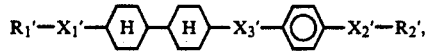

(VIc)
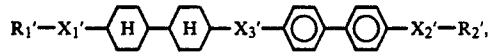

(VId)
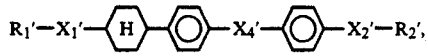

(VIe)
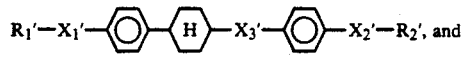

(VIf)
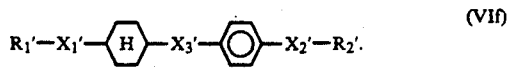

Herein, $R_1'$ and $R_2'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

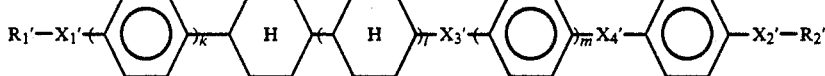

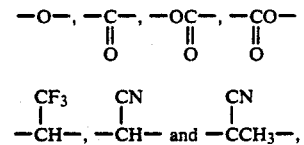

with proviso that $R_1'$ and $R_2'$ respectiely do not connect to a ring structure by a single bond when $R_1'$ and $R_2'$ respectively denote a halogenated alkyl group containing one methylene group replaced with —CH halogen— or —CH(CF$_3$)—.

Further, preferred examples of $R_1'$ and $R_2'$ may respectively include those represented by the following groups (i) to (ix):

i) a linear alkyl group having 1-15 carbon atoms;

ii) 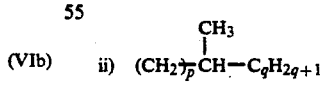

wherein p denotes an integer of 0-5 and q denotes an integer of 2-11 (optically active or inactive);

iii) 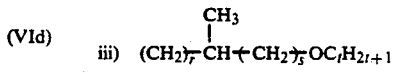

wherein r denotes an integer of 0-6, s denotes 0 or 1, and t denotes an integer of 1-14 (optically active or inactive);

iv) 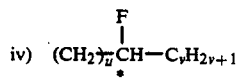

wherein u denotes 0 or 1 and v denotes an integer of 1–16;

v) 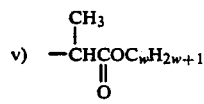

wherein w denotes an integer of 1–15 (optically active or inactive);

vi) 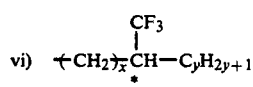

wherein x denotes an integer of 0–2 and y denotes an integer of 1–5.

vii) 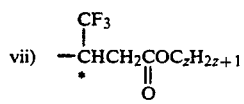

wherein z denotes an integer of 1–15.

viii) 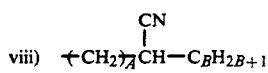

wherein A denotes an integer of 0–2 and B denotes an integer of 1–15 (optically active or inactive; and xi) 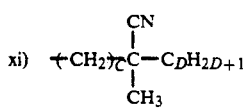

wherein C denotes an integer of 0–2 and D denotes an integer of 1–15 (optically active or inactive).

In the above-mentioned formula (III), more preferred compounds thereof may include those represented by the formulas (IIIaa) to (IIIdc):

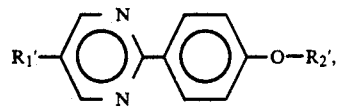 (IIIaa)

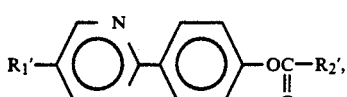 (IIIab)

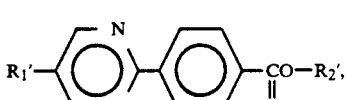 (IIIac)

-continued

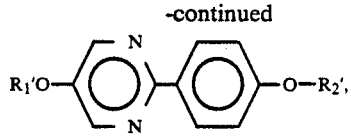 (IIIad)

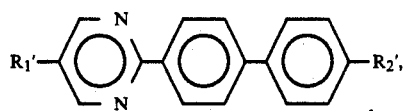 (IIIba)

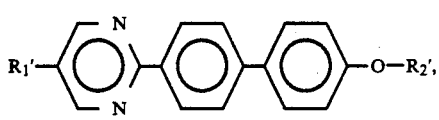 (IIIbb)

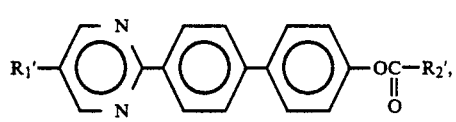 (IIIbc)

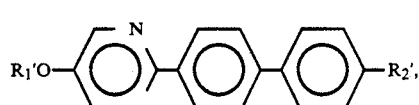 (IIIbd)

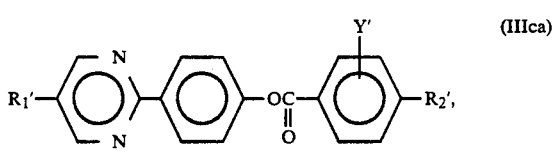 (IIIca)

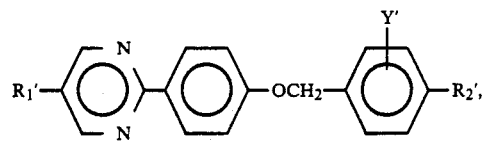 (IIIcb)

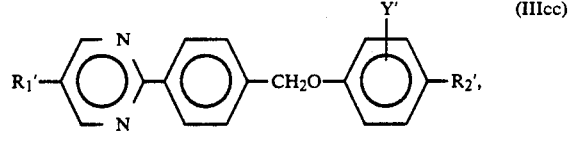 (IIIcc)

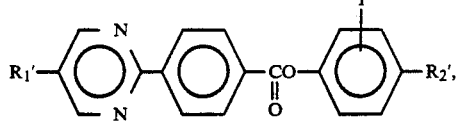 (IIIcd)

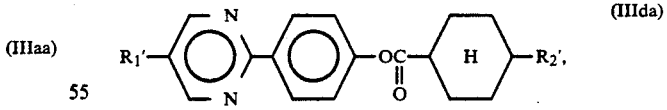 (IIIda)

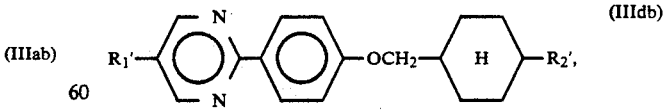 (IIIdb)

and

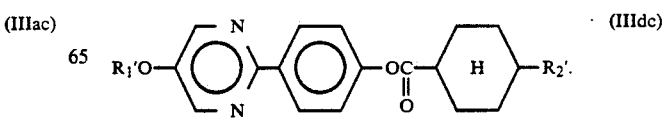 (IIIdc)

In the above-mentioned formula (IV), more preferred compounds thereof may include those represented by the formulas (IVaa) to (IVcd):

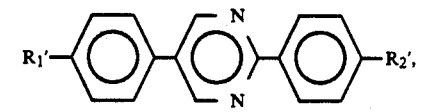 (IVaa)

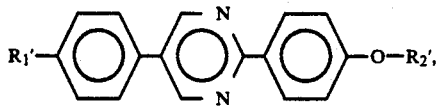 (IVab)

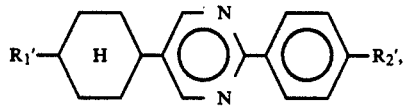 (IVba)

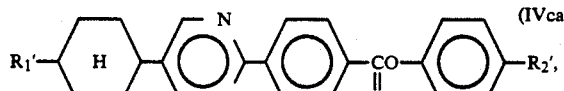 (IVca)

and

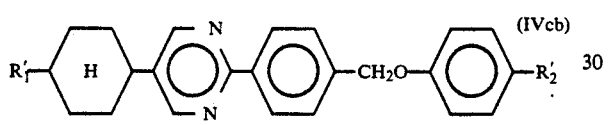 (IVcb)

In the above-mentioned formula (V), more preferred compounds thereof may include those represented by the formulas (Vaa) to (Vbf):

 (Vaa)

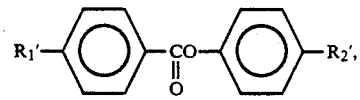 (Vab)

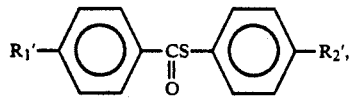 (Vac)

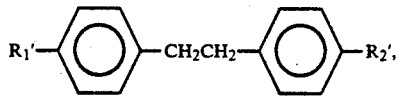 (Vad)

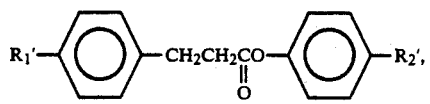 (Vae)

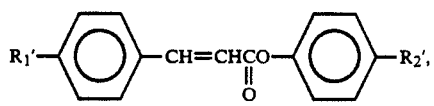 (Vaf)

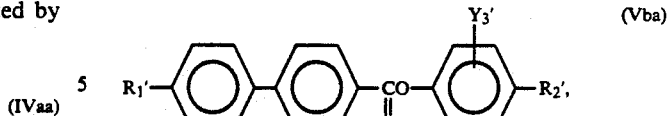 (Vba)

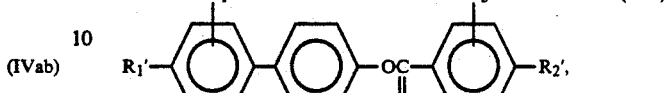 (Vbb)

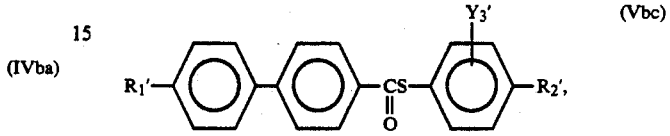 (Vbc)

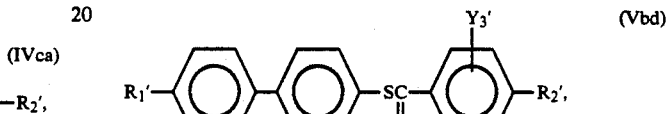 (Vbd)

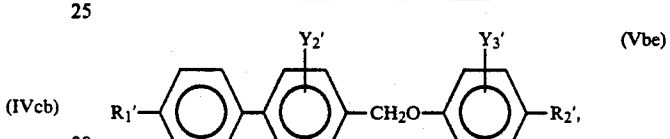 (Vbe)

and

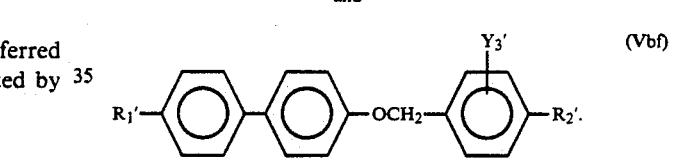 (Vbf)

In the above-mentioned formula (VI), more preferred compounds thereof may include those represented by the formulas (VIaa) to (VIfa):

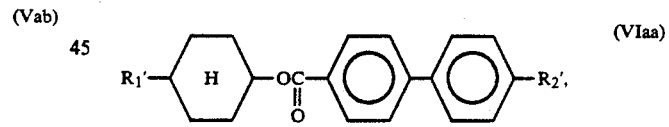 (VIaa)

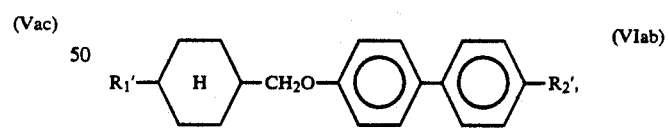 (VIab)

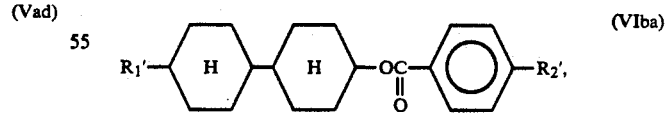 (VIba)

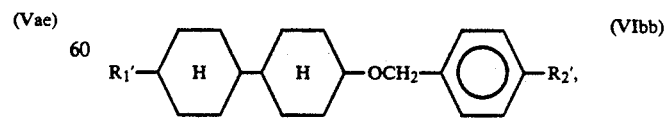 (VIbb)

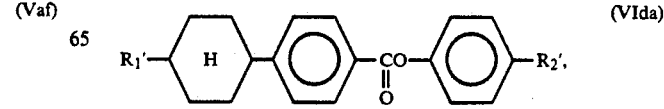 (VIda)

-continued

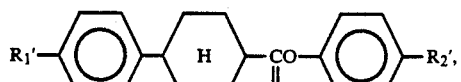
(VIea)

and

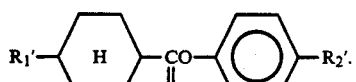
(VIfa)

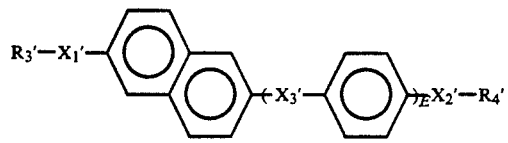
(VII)

wherein E denotes 0 or 1; $X_1'$ and $X_2'$ respectively denote a single bond,

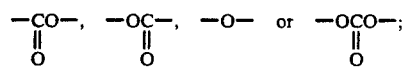

and $X_3'$ denotes a single bond,

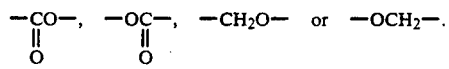

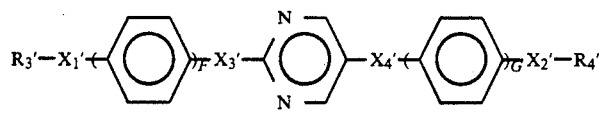
(VIII)

wherein F and G respectively denote 0 or 1; $X_1'$ and $X_2'$ respectively denote a single bond,

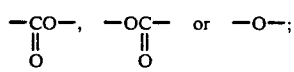

and $X_3'$ and $X_4'$ respectively denote a single bond,

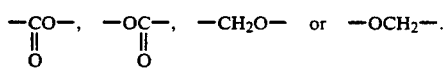

In the above formula (VII), preferred compounds thereof may include those represented by the following formulas (VIIa) and (VIIb):

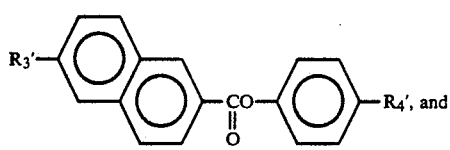
(VIIa)

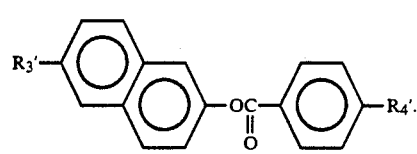
(VIIb)

In the above formula (VIII), preferred compounds thereof may include those represented by the following formulas (VIIIa) and (VIIIb).

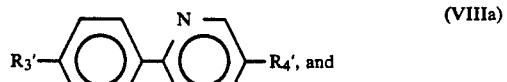
(VIIIa)

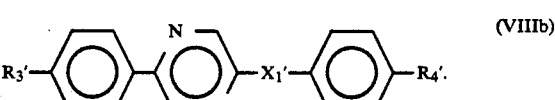
(VIIIb)

More preferred compounds of the formula (VIII) may include those represented by the formulas (VIIIba) to (VIIIbb):

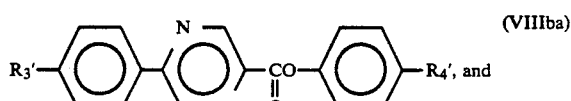
(VIIIba)

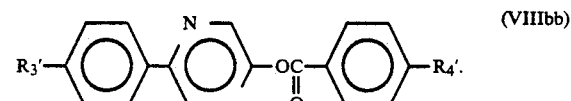
(VIIIbb)

Herein, $R_3'$ and $R_4'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

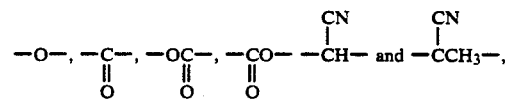

with proviso that $R_3'$ and $R_4'$ respectively do not connect to a ring structure by a single bond when $R_3'$ and $R_4'$ respectively denote a halogenated alkyl group containing one methylene group replaced with —CH halogen—.

Further, preferred examples of $R_3'$ and $R_4'$ may respectively include those represented by the following groups (i) to (vii):

i) a linear alkyl group having 1-15 carbon atoms;

ii) 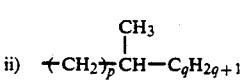

wherein p denotes an integer of 0-5 and q denotes an integer of 2-11 (optically active or inactive);

iii) 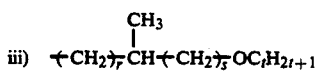

wherein r denotes an integer of 0-6, s denotes 0 or 1, and t denotes an integer of 1-14 (optically active or inactive);

iv) 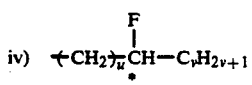

wherein u denotes an integer of 0 or 1 and v denotes an integer of 1-16;

v) 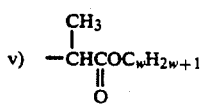

wherein w denotes an integer of 1-15 (optically active or inactive);

vi) 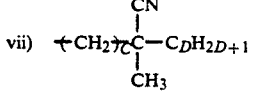

wherein A denotes an integer of 0-2 and B denotes an integer of 1-15 (optically active or inactive); and vii) 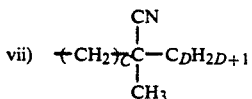

wherein C denotes an integer of 0-2 and D denotes an integer of 1-15 (optically active or inactive).

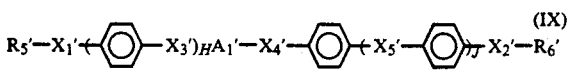 (IX)

wherein H and J respectively denote 0 or 1 with proviso that H+J=0 or 1; $X_1'$— and $X_2'$ respectively denote a single bond,

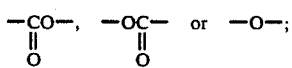

$A_1'$ denotes

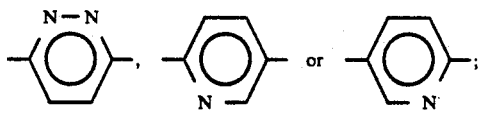

and $X_3'$ and $X_4'$ respectively denote a single bond,

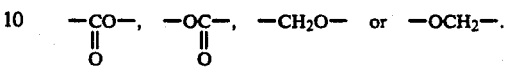

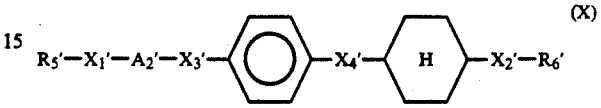 (X)

wherein $X_1'$ and $X_2'$ respectively denote a single bond,

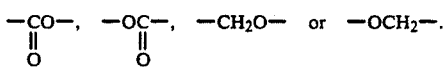

$A_2'$ denotes

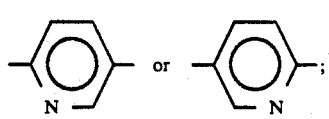

and $X_3'$ and $X_4'$ respectively denote a single bond,

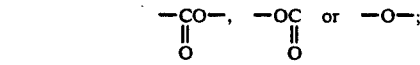

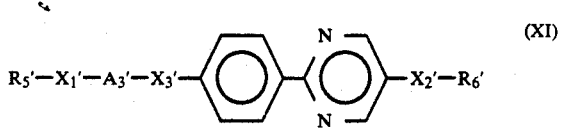 (XI)

wherein $X_1'$ and $X_2'$ respectively denote a single bond,

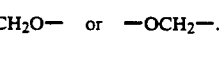

$A_3'$ denotes

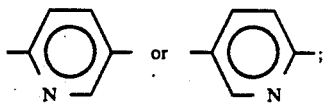

and $X_3'$ respectively denotes a single bond,

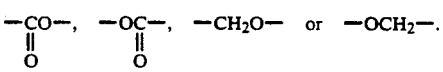

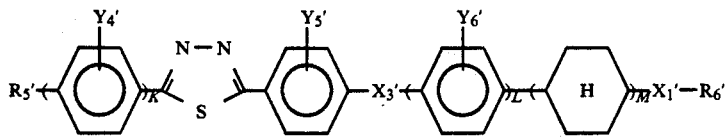

wherein K, L and M respectively denote 0 or 1 with the proviso that K+K+M=0 or 1; $X_1'$ denotes a single bond,

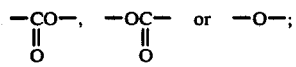

$X_3'$ denotes a single bond,

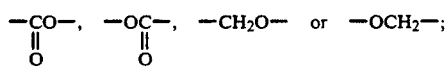

and $Y_4'$, $Y_5'$ and $Y_6'$ respectively denote H or F.

In the above formula (IX), preferred compounds thereof may include those represented by the following formulas (IXa) to (IXc):

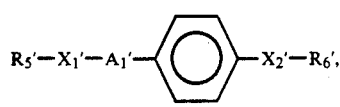

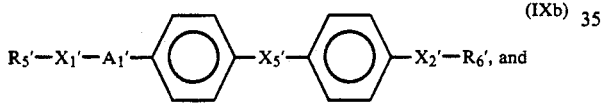

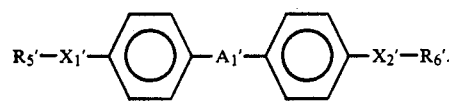

In the above formula (X), preferred compounds thereof may include those represented by the following formulas (Xa) and (Xb):

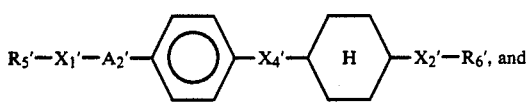

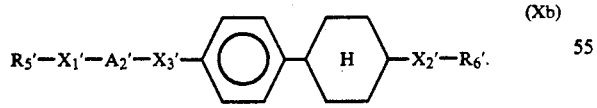

In the above formula (XII), preferred compounds thereof may include those represented by the following formulas (XIIa) and (XIId):

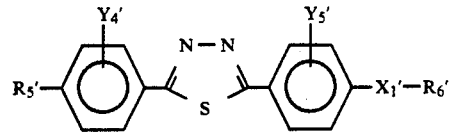

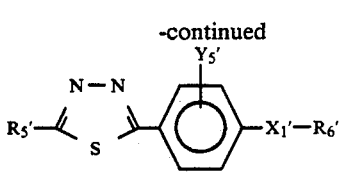

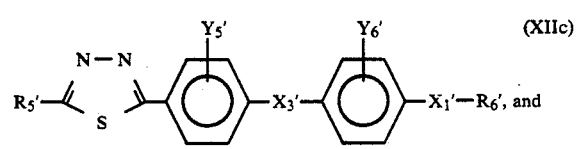

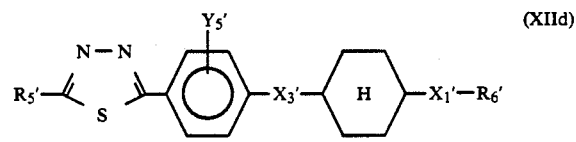

In the above-mentioned formula (IX), more preferred compounds thereof may include those represented by the formulas (IXaa) to (IXcc):

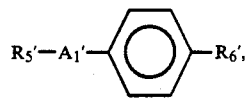

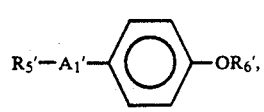

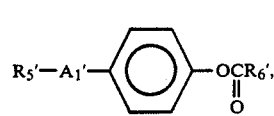

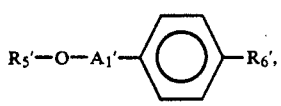

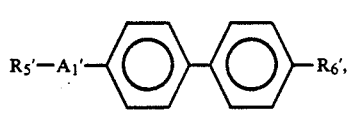

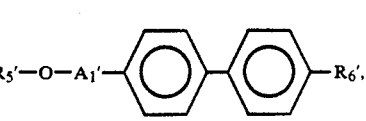

-continued

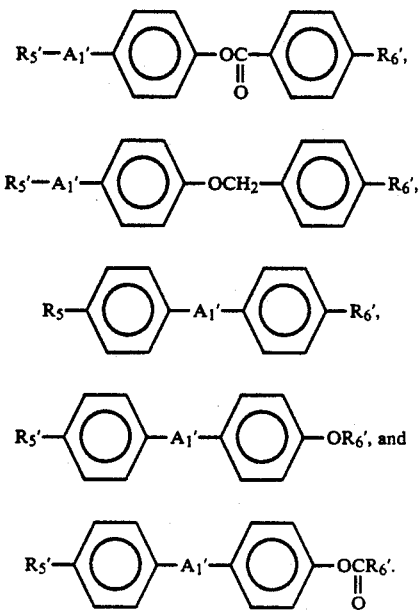

In the above-mentioned formula (X), more preferred compounds thereof may include those represented by the formulas (Xaa) to (Xbb):

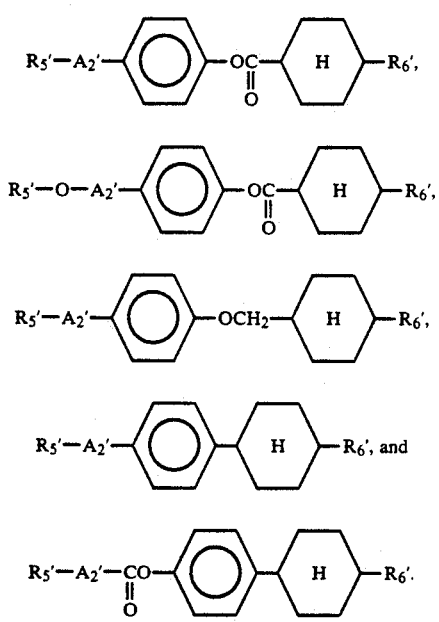

In the above formula (XI), preferred compounds thereof may include those represented by the following formulas (XIa) to (XIg):

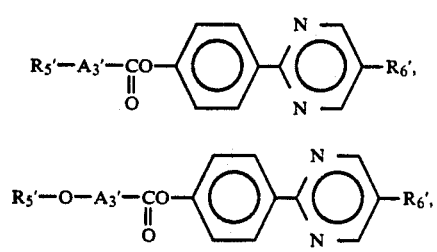

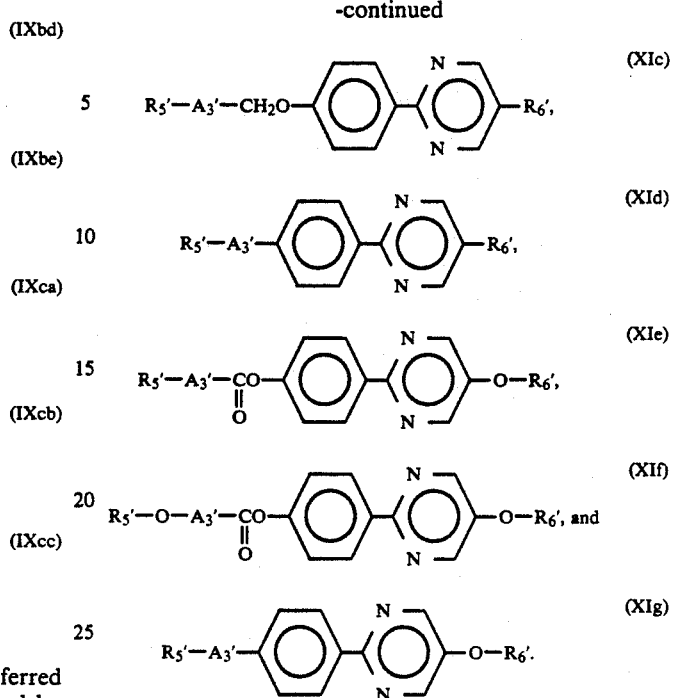

In the above-mentioned formula (XII), more preferred compounds thereof may include those represented by the formula (XIIaa) to (XIIdb):

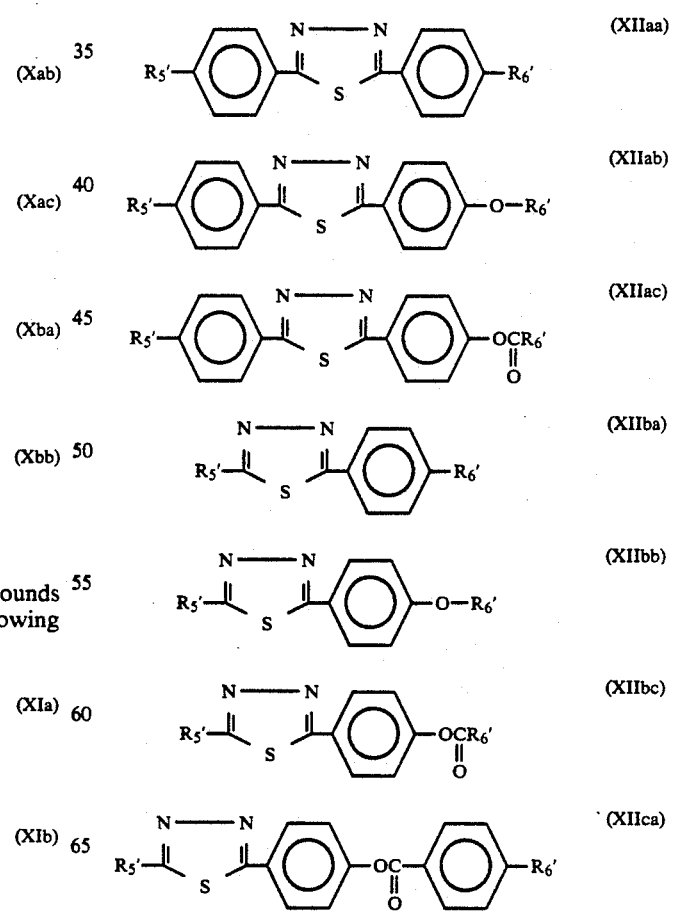

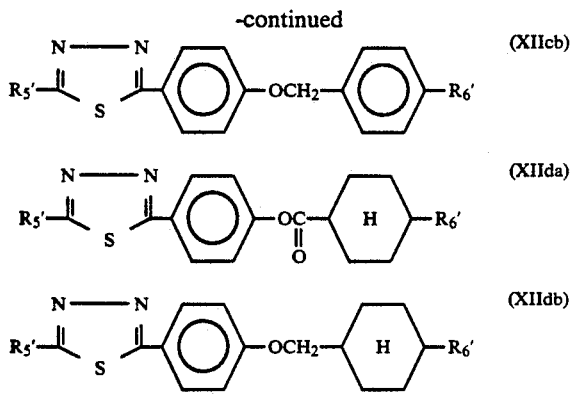

Herein, $R_5'$ and $R_6'$ respectively denote a linear or branched alkyl group having 1-18 carbon atoms capable of including one non-neighboring two or more methylene groups other than those directly connected to $X_1'$ or $X_2'$ which can be replaced with at least one species of

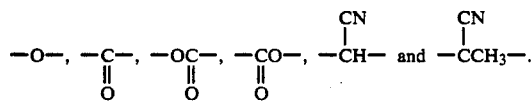

Further, preferred examples of $R_5'$ and $R_6'$ may respectively include those represented by the following groups (i) to (vi):

i) a linear alkyl group having 1-15 carbon atoms;

ii) 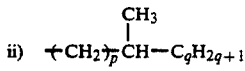

wherein p denotes an integer of 0-5 and q denotes an integer of 2-11 (optically active or inactive);

iii) 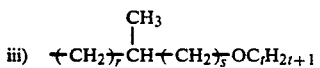

wherein r denotes an integer of 0-6, s denotes 0 or 1, and t denotes an integer of 1-14 (optically active or inactive);

iv) 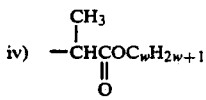

wherein w denotes an integer of 1-15 (optically active or inactive);

v) 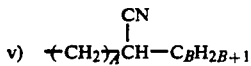

wherein A denotes an integer of 0-2 and B denotes an integer of 1-15 (optically active or inactive); and vi) 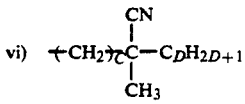

wherein C denotes an integer of 0-2 and D denotes an integer of 1-15 (optically active or inactive).

In formulating the liquid crystal composition according to the present invention, the liquid crystal composition may desirably contain 1-80 wt. %, preferably 1-60 wt. %, more preferably 1-40 wt. % of an opticall active compound represented by the formula (I).

Further, when two or more species of the compounds represented by the formula (I) are used, the liquid crystal composition may desirably contain 1-80 wt. %, preferably 1-60 wt. %, more preferably 1-40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure FIG. 1 is a schematic sectional view of an embodiment of the liquid crystal device utilizing ferroelectricity prepared as described above for explanation of the structure thereof Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of a applied voltage.

Figure 3:
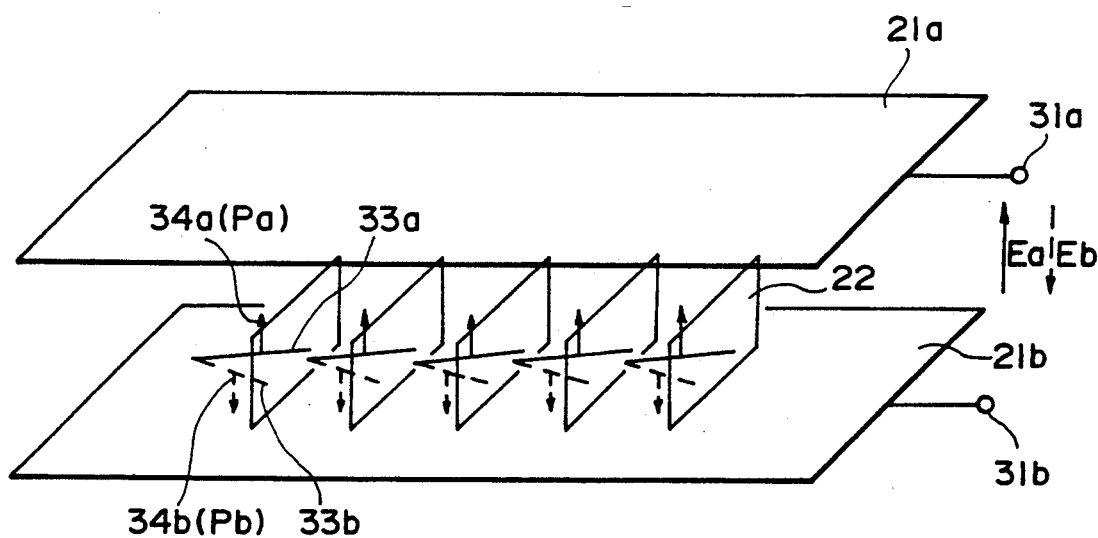

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3 When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly st ably retained even if the electric field is removed. Further, as long as the magnitude of the electric field Ea or Eb being applied is not above a certain threshold value, the liquid crystal molecules are placed in the respective orientation states.

Figure 4:
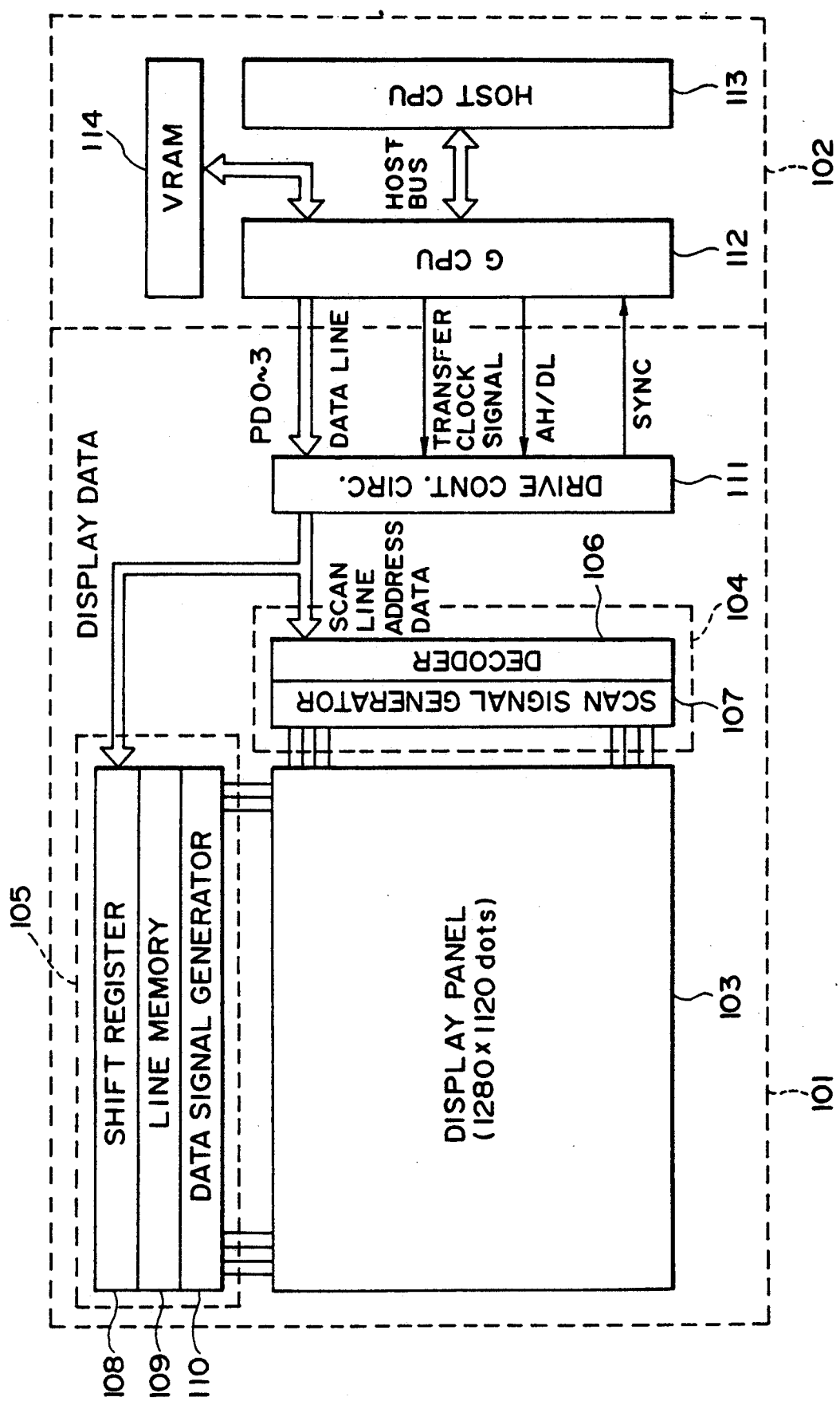
FIG. 4 is a block diagram showing a display apparatus comprising a liquid crystal device utilizing ferroelectricity of a liquid crystal composition and a graphic controller.
Figure 5:
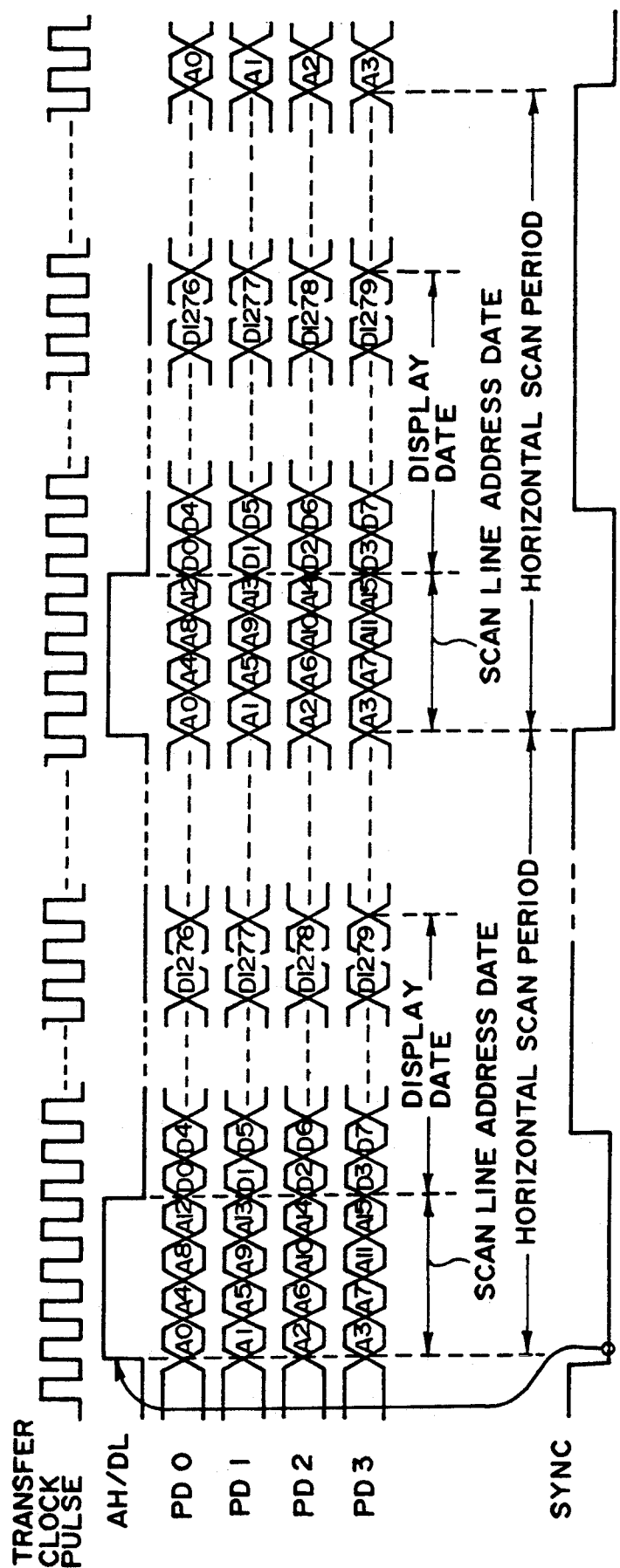
FIG. 5 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display pane) 103.

Hereinbelow, the present invention will be explained more specifically with reference to examples. It is however to be understood that the present invention is not restricted to these examples.

EXAMPLE 1

Production of optical active [4-{4-(3-trifluoromethylundecanoyloxy)phenyl}phenyl]-5-octyloxypyrimidine (Example Compound No. 94)

The above 2-[4-{4(3-trifluoromethylundecanoyloxy)phenyl}phenyl]-5-octyloxypyrimidine was synthesized through the following reaction scheme.

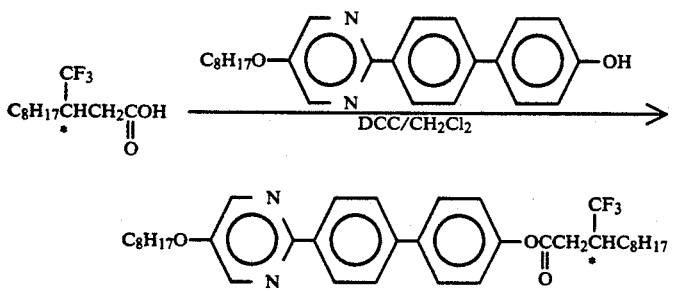

0.38 g (1 mM) of 2-{4-(4-hydroxyphenyl)phenyl}-5-octyloxypyrimidine, 0.2 g (1 mM) of 3-tifluoromethylundecanoic acid, 0.21 g of N,N'-dicyclohexylcarbodiimide (DCC) and 0.02 g of 4-pyrrolidinopyridine were dissolved in 12 ml of dichloromethane, followed by stirring overnight at room temperature. After the reaction, the reaction mixture was subjected to filtration, whereby the insoluble matter was removed. The resultant filtrate was purified by silica gel column chromatography (eluent: toluene) and recrystallized from a mixture solvent (methanol/toluene) to obtain 0.38 g of an objective product (Yield: 61%).

Phase transition temperature (°C.)

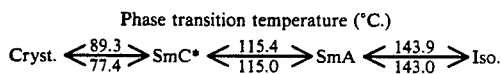

Herein, the respective symbols denote the following phase; Iso: isotropic phase; SmA: smectic A phase; SmC*: chiral smectic C phase; and Cryst.: crystal.

EXAMPLE 2

Production of optically active 2-{4-(3-trifluoromethylundecanoyloxy)phenyl}-5-(4-octyloxyphenyl)-pyrimidine (Example Compound No. 82)

The above 2-(4-(3-trifluoromethylundecanoyl-oxy)-phenyl}pyrimidine was synthesized through the following reaction scheme.

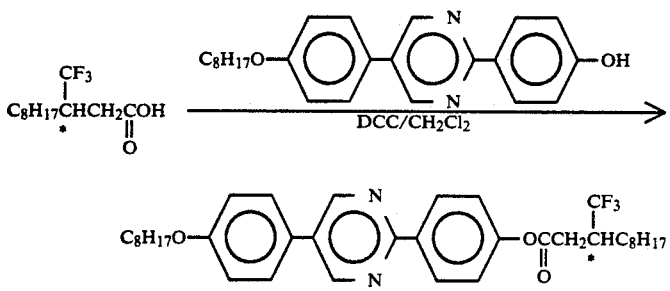

An objective product was synthesized in the same manner as in Example 1 except for using 2-(4-hydroxyphenyl)-5-(4-octyloxyphenyl)pyrimidine instead of 2-(4-(4-hydroxyphenyl)phenyl}-5-octyloxypyrimidine (Yield: 56%).

Phase transition temperature (°C.)

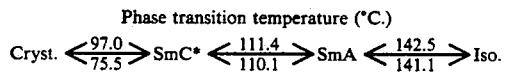

EXAMPLE 3

Production of optically active 2-{4-(3-trifluoromethylnonanoyloxy)phenyl}-5-(4-octyloxyphenyl)pyrimidine (Example Compound No. 84)

The above compound was synthesized through the following reaction scheme.

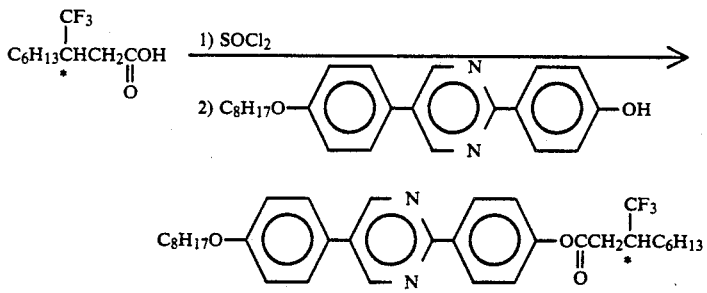

In a 30 ml-round-bottomed flask, 190 mg (0.84 mM) of (+)-3-trifluoromethylnonanoic acid and 1 ml of thionyl chloride were placed, followed by heating for 1.5 hours at 90° C. After the reaction, excessive thionyl chloride was removed by using component distillation with benzene. 2 ml of dry tetrahydrofuran (THF), 263 mg (0.70 mM) of 2-(4-hydroxyphenyl)-5-(4-octyloxyphenyl)pyrimidine and a solution of 116 mg (1.1 mM) of triethylenediamine in dry benzene were added to the resultant residue, followed by stirring for 30 minutes at room temperature, heating for 2 hours at 50° C., stirring overnight at room temperature and heating 3 hours at 70° C., successively. After the reaction, 2 ml of 3M hydrochloric acid and 10 ml of water were added to the reaction mixture, followed by extraction with benzene and drying with anhydrous sodium sulfate. The solvent was distilled-off under reduced pressure from the resultant mixture, followed by purification by thin-layer chromatography (developing solvent: hexane/ethyl acetate =3/1) to obtain 365 mg (0.63 mM) of 2-{4-(3-trifluoromethylnonanoyloxy)phenyl}-5-(4-octyloxyphenyl)pyrimidine (Yield: 89.3%).

Phase transition temperature (°C.)

Cryst. ⇄ 75/74 → SmC* ⇄ 125/124 → SmA ⇄ 151/151 → Iso.

EXAMPLE 4

Production of optically active 2-[4-{4-(3-trifluoromethylnonanoyloxy)phenyl}phenyl]-5-octyloxypyrimidine (Example Compound No. 88)

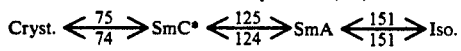

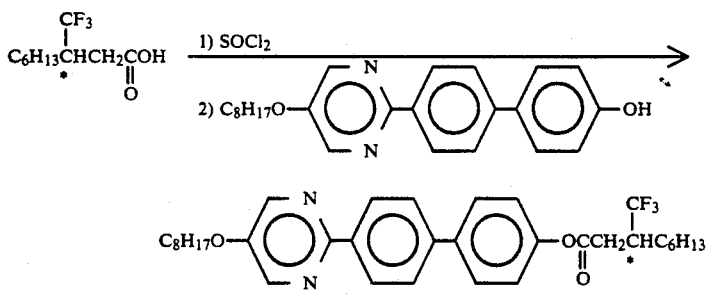

An objective product was synthesized in the same manner as in Example 3 except for using 2-{4-(4-hydroxyphenyl)phenyl}-5-octyloxypyrimidine instead of 2-(4-hydroxyphenyl)-5-(4-octyloxyphenyl)pyrimidine (Yield: 70%).

Phase transition temperature (°C.)

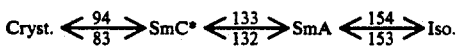

Cryst. ⇄ 94/83 → SmC* ⇄ 133/132 → SmA ⇄ 154/153 → Iso.

EXAMPLE 5

Production of optically active 2-{4-(3-trifluoromethylnonanoyloxy)phenyl}-5-(4-octylphenyl)pyrimidine (Example Compound No. 90)

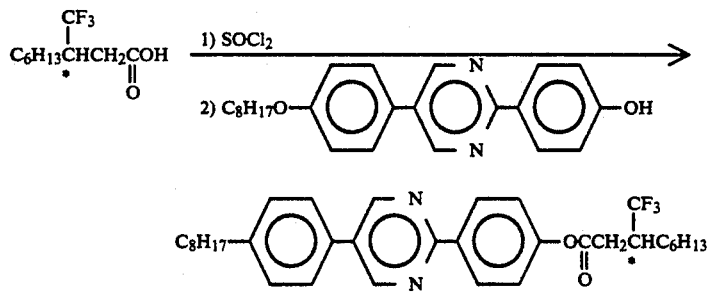

An objective product was synthesized in the same manner as in Example 3 except for using 2-(4-hydroxyphenyl)-5-(4-octyloxyphenyl)pyrimidine instead of 2-(4-hydroxyphenyl)-5-(4-octyloxyphenyl)pyrimidine (Yield: 69%).

Phase transition temperature (°C.)

Cryst. ⇄ 89.0/69.0 → SmC* ⇄ 103.5/102.0 → SmA ⇄ 132.0/130.0 → Iso.

EXAMPLE 6

Production of optically active 2-(4-(3-trifluoromethylheptanoyloxy)phenyl}-5-(4-octyloxyphenyl)-pyrimidine (Example Compound No. 85)

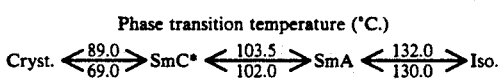

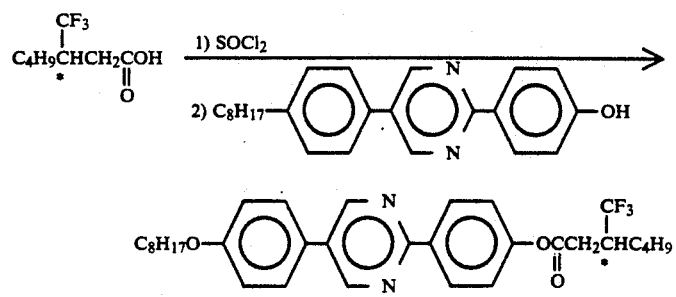

An objective product was synthesized in the same manner as in Example 3 except for using 3-trifluoromethylheptanoic acid instead of 3-trifluoromethylnonanoic acid (Yield: 34%).

Phase transition temperature (°C.)

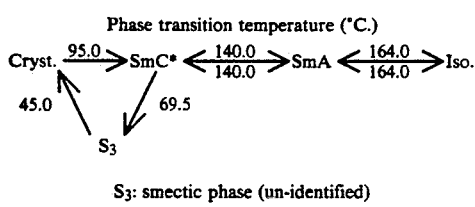

S3: smectic phase (un-identified)

EXAMPLE 7

Production of optically active 2-{4-(3-trifluoromethylnonanoyloxy)phenyl]-5-(4-octyloxyphenyl)pyrimidine (Example Compound No. 83)

The above compound was synthesized through the following steps i) and ii).

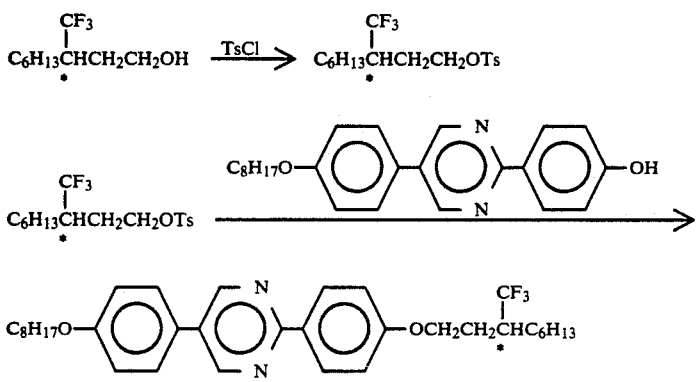

Step i)

To a mixture of 550 mg (2.6 mM) of (+)-3-trifluoromethyl-1-nonanoyl and 790 mg (10 mM) of pyridine, 500 mg (2.62 mM) of p-toluenesulfonyl chloride, followed by stirring for 2 hours at room temperature. After the reaction, the reaction mixture was neutralized with 2M-hydrochloric acid and extracted with methylene chloride to obtain 820 mg of 3-trifluoromethyl-nonyltosylate.

Step ii)

In a 30 ml-round-bottomed flask, a solution of 0.188 g (0.50 mM) of 2-(4-hydroxyphenyl)-5-(4-octyloxyphenyl)pyrimidine in dry THF and 2 ml of dry N,N-dimethylformamide were placed and sufficiently stirred. To the mixture, 40 mg of 60%-sodium hydride was added and 0.183 g (0.50 mM) of (−)-3-trifluoromethylnonyl p-toluene sulfonate was further added dropwise, followed by stirring for 6 hours at 130° C. After the reaction, distilled water was added to the reaction mixture and extracted with ether, followed by drying with anhydrous sodium sulfate and purification by thin-layer chromatography (developing solvent: hexane/ethyl acetate =3/1 (first) and 4/1 (second)) to obtain 0.13 g (0.23 mM) of 2-{4-(3-trifluoromethylnonyloxy)phenyl}-5-(4-octyloxyphenyl)pyrimidine (Yield: 46.0%).

Phase transition temperature (°C.)

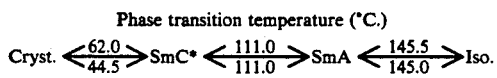

EXAMPLE 8

Production of optically active 2-[4-{4-(3-trifluoromethylnonyloxy)phenyl}phenyl]-5-octyloxypyrimidine (Example Compound No. 39)

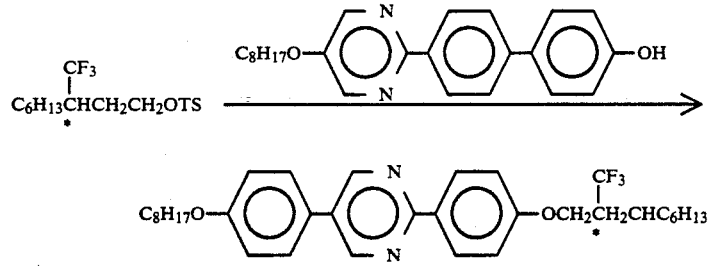

An objective product was synthesized in the same manner as in Example 7 except for using 2-(4-(4-hydroxyphenyl)phenyl}-5-octylOxypyrimidine instead of 2-(4-hydroxyphenyl)-5-(4-octyloxyphenyl)pyrimidine (Yield: 24%).

Phase transition temperature (°C.)

Cryst. ⇄ 69.5/49.0 ⇄ S4 ⇄ 103.0/86.0 ⇄ S3 ⇄ 107.0/101.0 ⇄ SmC* ⇄ 111.0/111.0 ⇄ SmA ⇄ 144.5/143.0 ⇄ Iso.

S4: smectic phase (un-identified)

EXAMPLE 9

A liquid crystal composition A was prepared by mixing the following compounds in the respectively indicated proportions.

| Structural formula | wt. parts |
|---|---|
| 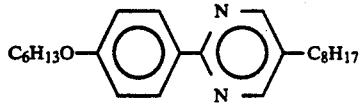 | 48.57 |
| 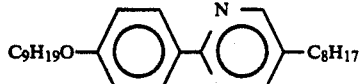 | 24.29 |
| 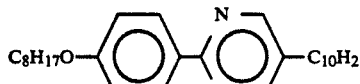 | 12.14 |
| 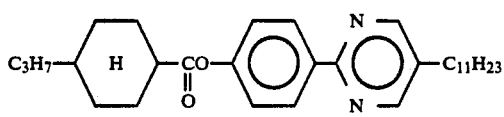 | 3.75 |
| 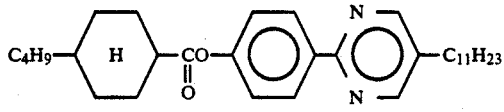 | 3.75 |
| 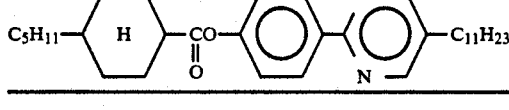 | 7.5 |

The liquid crystal composition A aws further mixed with the following Example Compound No. 94 in the proportions indicated below to provide a liquid crystal composition B.

EXAMPLE 10

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 9 was heated into an isotropic liquid, and injected into the above prepared cell under vacuum and, after sealing, was gradually cooled at a rate of 20° C./hour to 25° C. to prepare a ferroelectric liquid crystal device.

Each of the ferroelectric liquid crystal devices was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

| Ex. Comp. No. | Structural Formula | wt. parts |
|---|---|---|
| 94 | 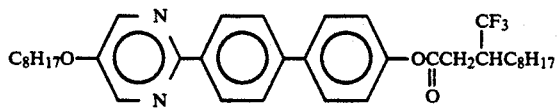 | 5 |
| | Composition A | 95 |

The liquid crystal composition B showed the following phase transition series.

Phase transition temperature (°C.)

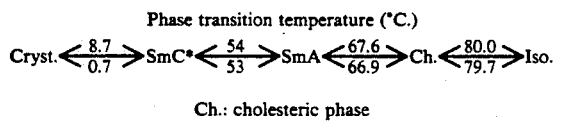

Ch.: cholesteric phase

| | 25° C. | 30° C. | 40° C. |
|---|---|---|---|
| Response time (μsec) | 268 | 213 | 141 |
| Ps (nC/cm²) | 2.9 | 2.7 | 2.5 |

EXAMPLE 11

A liquid crystal composition C was prepared by mixing the following Example Compound No. 84 prepared in Example 3 in the indicated proportions with the liquid crystal composition A prepared in Example 9.

| Ex. Comp. No. | Structural Formula | wt. parts |
|---|---|---|
| 84 | C$_8$H$_{17}$O—⬡—(N=N)—⬡—OCCH$_2$CHC$_6$H$_{13}$ with CF$_3$, O | 5 |
| | Composition A | 95 |

The liquid crystal composition C showed the following phase transition series.

Phase transition temperature (°C.)

Cryst. $\xrightarrow[0.2]{8.9}$ SmC* $\xrightarrow[53]{54}$ SmA $\xrightarrow[70.8]{71.6}$ Ch. $\xrightarrow[80.7]{80.8}$ Iso.

A ferroelectric liquid crystal device was prepared in the same manner as in Example 10 except for using the composition C. The ferroelectric liquid crystal device was subjected to measurement of the magnitude of spontaneous polarization Ps and response time in the same manner as in Example 10, whereby the following results were obtained.

| | 25° C. | 30° C. | 40° C. |
|---|---|---|---|
| Response time (μsec) | 254 | 202 | 134 |
| Ps (nC/cm$^2$) | 2.8 | 2.7 | 2.0 |

EXAMPLE 12

A liquid crystal composition D was prepared by mixing the following Example Compound No. 88 prepared in Example 4 in the indicated proportions with the liquid crystal composition A prepared in Example 9.

| Ex. Comp. No. | Structural Formula | wt. parts |
|---|---|---|
| 88 |  | 5 |
| | Composition A | 95 |

The liquid crystal composition D showed the following phase transition series.

Phase transition temperature (°C.)

Cryst. $\xrightarrow[1.2]{9.5}$ SmC* $\xrightarrow[54]{55}$ SmA $\xrightarrow[67.5]{68.2}$ Ch. $\xrightarrow[80.1]{80.5}$ Iso.

A ferroelectric liquid crystal device was prepared in the same manner as in Example 10 except for using the composition D. The ferroelectric liquid crystal device was subjected to measurement of the magnitude of spontaneous polarization Ps and response time in the same manner as in Example 10, whereby the following results were obtained.

| | 25° C. | 30° C. | 40° C. |
|---|---|---|---|
| Response time (μsec) | 302 | 245 | 160 |
| Ps (nC/cm$^2$) | 2.7 | 2.4 | 1.9 |

EXAMPLE 13

A liquid crystal composition E was prepared by mixing the following Example Compound No. 90 prepared in Example 5 in the indicated proportions with the liquid crystal composition A prepared in Example 9.

| Ex. Comp. No. | Structural Formula | wt. parts |
|---|---|---|
| 90 | C$_8$H$_{17}$O—⬡—(N=N)—⬡—⬡—OCCH$_2$CHC$_6$H$_{13}$ with CF$_3$, O | 5 |
| | Composition A | 95 |

The liquid crystal composition E showed the following phase transition series.

Phase transition temperature (°C.)

Cryst. $\xrightarrow[0.2]{8.9}$ SmC* $\xrightarrow[56.0]{57.0}$ SmA $\xrightarrow[67.5]{68.3}$ Ch. $\xrightarrow[78.1]{78.6}$ Iso.

A ferroelectric liquid crystal device was prepared in the same manner as in Example 10 except for using the composition E. The ferroelectric liquid crystal device was subjected to measurement of the magnitude of spontaneous polarization Ps and response time in the same manner as in Example 10, whereby the following results were obtained.

| | 25° C. | 30° C. | 40° C. |
|---|---|---|---|
| Response time (μsec) | 312 | 251 | 168 |
| Ps (nC/cm$^2$) | 2.3 | 2.1 | 1.8 |

COMPARATIVE EXAMPLE 1

A liquid crystal composition F was prepared by mixing the following compound in the indicated proportion with the liquid crystal composition A prepared in Example 9.

| Structural Formula | wt. parts |
|---|---|
| 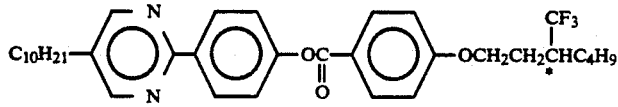 | 5 |
| Composition A | 95 |

The liquid crystal composition F showed the following phase transition series.

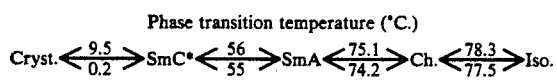

A ferroelectric liquid crystal device was prepared in the same manner as in Example 10 except for using the composition F. The ferroelectric liquid crystal device was subjected to measurement of the magnitude of spontaneous polarization Ps and response time in the same manner as in Example 10, whereby the following results were obtained.

| | 25° C. | 30° C. | 40° C. |
|---|---|---|---|
| Response time ($\mu$sec) | 461 | 348 | 211 |
| Ps (nC/cm$^2$) | 2.7 | 2.4 | 1.9 |

As is apparent from the above Examples 1-13 and Comparative Example 1, the liquid crystal compositions B-E each having three rings as a mesogen skeleton connected by a single bond to one another provided a high-speed responsiveness and a decreased temperature dependence of response speed compared with the liquid crystal composition F having three rings containing a ester linkage.

As described hereinabove, according to the present invention, there is provided an optically active compound which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. An optically active compound represented by the following formula (I):

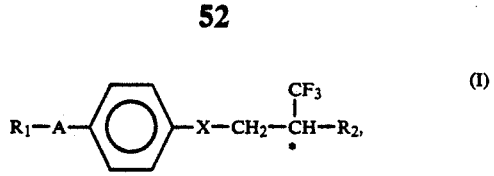

wherein $R_1$ denotes an alkyl or alkoxy group having 1-18 carbon atoms; $R_2$ denotes an alkyl group having 1-12 carbon atoms; A denotes

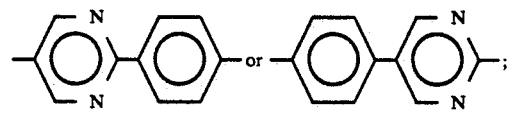

X denotes

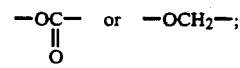

and C* denotes an optically active asymmetric carbon atom.

2. An optically active compound according to claim 1, wherein $R_1$ denotes an alkyl or alkoxy group having 3-14 carbon atoms and $R_2$ denotes an alkyl group having 4-8 carbon atoms.

3. An optically active compound according to claim 1, which is a mesomorphic compound.

4. An optical active compound according to claim 1, which has a chiral smectic phase.

5. A liquid crystal composition comprising at least two compounds, at least one of which is an optically active compound of the formula (I) according to claim 1.

6. A liquid crystal composition according to claim 5, which comprises 1-80 wt. % of an optically active compound of the formula (I).

7. A liquid crystal composition according to claim 5, which comprises 1-60 wt. % of an optically active compound of the formula (I).

8. A liquid crystal composition according to claim 5, which comprises 1-40 wt. % of an optically active compound of the formula (I).

9. A liquid crystal composition according to claim 5, which has a chiral smectic phase.

10. A liquid crystal device, comprising a pair of electrode plates and a liquid crystal composition according to claim 5 disposed between the electrode plates.

11. A liquid crystal device according to claim 10, which further comprises an insulating alignment control layer.

12. A liquid crystal device according to claim 11, wherein the insulating alignment control layer has been subjected to rubbing.

13. A liquid crystal device according to claim 10, wherein the liquid crystal composition is disposed in a thickness suppressing formation of a helical structure of liquid crystal molecules between the electrode plates.

14. A display apparatus comprising a liquid crystal device according to claim 10, and voltage application means for driving the liquid crystal device.

15. A display apparatus according to claim 14, which further comprises a drive circuit.

16. A display apparatus according to claim 15, which further comprises a light source.

17. A display method, comprising:
providing a liquid crystal composition comprising at least two compounds, at least one of which is an optically active compound of the formula (I) according to claim 1; and
switching the alignment direction of liquid crystal molecules by applying voltages to the liquid crystal composition to effect display.

18. A display method according to claim 17, wherein $R_1$ in the formula (I) denotes an alkyl or alkoxy group having 3-14 carbon atoms and $R_2$ denotes an alkyl group having 4-8 carbon atoms.

19. A display method according to claim 17 wherein the optically active compound of the formula (I) is a mesomorphic compound.

20. A display method according to claim 17, wherein the optically active compound has a chiral smectic phase.

21. A display method according to claim 17, wherein the liquid crystal composition comprises 1-80 wt. % of an optically active compound of the formula (I).

22. A display method according to claim 17, wherein the liquid crystal composition comprises 1-60 wt. % of an optically active compound of the formula (I).

23. A display method according to claim 17, wherein the liquid crystal composition comprises 1-40 wt. % of an optically active compound of the formula (I).

24. A display method according to claim 17, wherein the liquid crystal composition has a chiral smectic phase.

25. A display method, comprising:
providing a liquid crystal device comprising a pair of electrode plates and a liquid crystal composition disposed therebetween comprising at least two compounds, at least one of which is an optically active compound of the formula (I) according to claim 1; and
switching the alignment direction of liquid crystal molecules by applying voltages to the liquid crystal composition disposed between the electrode plates to effect display.

26. A display method according to claim 25, wherein the liquid crystal device further comprises an insulating alignment control layer.

27. A display method according to claim 26, wherein the insulating alignment control layer has been subjected to rubbing.

28. A display method according to claim 25, wherein the liquid crystal composition is disposed in a thickness suppressing formation of a helical structure of liquid crystal molecules between the electrode plates.

* * * * *

UNITED STATES PATENT AND TRADEMARK OFFICE
CERTIFICATE OF CORRECTION

PATENT NO. : 5,281,362
DATED : January 25, 1994
INVENTOR(S) : HIROYUKI NOHIRA, ET AL.

It is certified that error appears in the above-identified patent and that said Letters Patent is hereby corrected as shown below:

ON TITLE PAGE

In [56] References Cited, under FOREIGN PATENT DOCUMENTS:
"1-31131  5/1989  Japan" should read
--131131  5/1989  Japan--.

COLUMN 1

Line 62, "are," should read --is,--.

COLUMN 2

Line 3, "is" should read --are--.
Line 33, "electric" should read --electric field--.

COLUMN 3

Line 7, "bistability" should read --bistability.--.

COLUMN 4

Line 57, "4/1988" should read --37624/1988--.

COLUMN 5

Lines 15-25, " 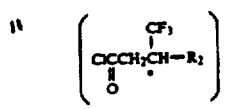 " should read -- 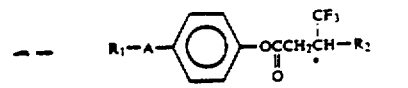

or

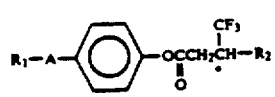 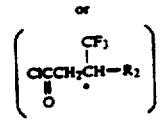 --.

UNITED STATES PATENT AND TRADEMARK OFFICE
CERTIFICATE OF CORRECTION

PATENT NO. : 5,281,362
DATED : January 25, 1994
INVENTOR(S) : HIROYUKI NOHIRA, ET AL.

It is certified that error appears in the above-identified patent and that said Letters Patent is hereby corrected as shown below:

COLUMN 6

Formula (2), "$C_6H_{11}$" should read --$C_5H_{11}$--.
Formula (3), "$C_6H_{11}$" should read --$C_6H_{13}$--.

COLUMN 24

Line 45, "respectiely" should read --respectively--.

COLUMN 25

Line 39, "inactive;" should read --inactive);--.

COLUMN 33

Line 11, "K+K+M" should read --K+L+M--.

COLUMN 36

Line 31, "formula" should read --formulas--.

COLUMN 38

Line 25, "thereof" should read --thereof.--.

COLUMN 39

Line 56, "a" should read --an--.

COLUMN 40

Line 21, "st ably" should read --stably--.

UNITED STATES PATENT AND TRADEMARK OFFICE
CERTIFICATE OF CORRECTION

PATENT NO. : 5,281,362
DATED : January 25, 1994
INVENTOR(S) : HIROYUKI NOHIRA, ET AL.

Page 3 of 4

It is certified that error appears in the above-identified patent and that said Letters Patent is hereby corrected as shown below:

COLUMN 41

Line 52, "2-(4-(3-" should read --2-{4-(3- --.

COLUMN 45

Line 13, "phenyl]" should read --phenyl}--.
Line 37, "chloride," should read --chloride was added,--.

COLUMN 46

Line 53, "2-(4-(4-" should read --2-{4-(4- --.
Line 54, "octylOxypyrimidine" should read --octyloxypyrimidine--.

COLUMN 47

Line 40, "aws" should read --was--.

COLUMN 48

Line 8, "K" should read --K.--.

COLUMN 50

Line 29, "$C_8H_{17}O$" should read --$C_8H_{17}$--.

COLUMN 52

Line 43, "optical" should read --optically--.

UNITED STATES PATENT AND TRADEMARK OFFICE
CERTIFICATE OF CORRECTION

PATENT NO.  : 5,281,362
DATED       : January 25, 1994
INVENTOR(S) : HIROYUKI NOHIRA, ET AL.

It is certified that error appears in the above-identified patent and that said Letters Patent is hereby corrected as shown below:

<u>COLUMN 53</u>

Line 28, "claim 17" should read --claim 17,--.

Signed and Sealed this

Thirtieth Day of August, 1994

Attest:

BRUCE LEHMAN

Attesting Officer    Commissioner of Patents and Trademarks